(12) United States Patent
Kasahara et al.

(10) Patent No.: US 8,016,821 B2
(45) Date of Patent: Sep. 13, 2011

(54) LIVING BODY TISSUE HARVESTING APPARATUS

(75) Inventors: Hideyuki Kasahara, Hachioji (JP); Takahiro Kogasaka, Hachioji (JP); Takumi Dejima, Mitaka (JP); Manabu Miyamoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 1292 days.

(21) Appl. No.: 11/646,958

(22) Filed: Dec. 28, 2006

(65) Prior Publication Data

US 2007/0185481 A1 Aug. 9, 2007

Related U.S. Application Data

(63) Continuation-in-part of application No. 11/453,329, filed on Jun. 14, 2006, which is a continuation of application No. PCT/JP2005/017491, filed on Sep. 22, 2005.

(30) Foreign Application Priority Data

Sep. 22, 2004 (JP) ................................. 2004-275747
Sep. 22, 2004 (JP) ................................. 2004-275752

(51) Int. Cl.
*A61B 18/18* (2006.01)
(52) U.S. Cl. ............................. 606/37; 606/45; 606/39
(58) Field of Classification Search ............... 606/37–52
See application file for complete search history.

(56) References Cited

U.S. PATENT DOCUMENTS

| 4,971,034 | A | 11/1990 | Doi et al. | |
|---|---|---|---|---|
| 5,895,353 | A | 4/1999 | Lunsford et al. | |
| 6,165,175 | A * | 12/2000 | Wampler et al. | 606/48 |
| 6,514,215 | B1 | 2/2003 | Ouichi | |
| 6,656,176 | B2 * | 12/2003 | Hess et al. | 606/51 |
| 2003/0130654 | A1 * | 7/2003 | Kasahara et al. | 606/45 |

FOREIGN PATENT DOCUMENTS

| GB | 2 198 948 A | 6/1988 |
|---|---|---|
| JP | 51-122987 | 3/1976 |
| JP | 55-40533 | 3/1980 |
| JP | 63-161929 | 7/1988 |
| JP | 05-285094 | 11/1993 |
| JP | 6-67387 | 8/1994 |
| JP | 2001-120556 | 5/2001 |
| JP | 2002-305010 | 10/2002 |
| JP | 2003-000534 | 1/2003 |
| JP | 2004-008241 | 1/2004 |
| JP | 2004-159687 | 6/2004 |

* cited by examiner

*Primary Examiner* — Linda Dvorak
*Assistant Examiner* — Amanda Scott
(74) *Attorney, Agent, or Firm* — Scully, Scott, Murphy & Presser, P.C.

(57) ABSTRACT

In a bipolar cutter for a living body tissue, a groove part is formed in a member that is arranged close to an active electrode, thereby providing a constitution to cut while the blood stanching is ensured since when a heat amount generated by the active electrode is conducted in the member, an excessive heat conduction to the member is efficiently interrupted by a layer of air that is produced due to the groove part and the living tissue is thus provided with more heat.

16 Claims, 34 Drawing Sheets

LIVING BODY TISSUE HARVESTING APPARATUS

CROSS REFERENCES TO RELATED APPLICATIONS

This application is a continuation-in-part of U.S. application Ser. No. 11/453,329 filed on Jun. 14, 2006 which is a continuation application of PCT/JP2005/017491 filed on Sep. 22, 2005 and claims benefit of Japanese Patent Applications No. 2004-275747 filed in Japan on Sep. 22, 2004 and No. 2004-275752 filed in Japan on Sep. 22, 2004, the entire contents of which are incorporated herein by this reference.

BACKGROUND OF THE INVENTION

1. Field of the Invention

The present invention relates to a living body tissue harvesting apparatus for pulling and harvesting living body tissues such as a subcutaneous vessel under endoscopic observation.

2. Description of the Related Art

In a bypass surgery of a blood vessel of heart in recent years, a vessel of a lower limb of a patient that is his/her own great saphenous vein or the like is occasionally used. A living body tissue harvesting apparatus for harvesting such vessel of the lower limb under endoscopic observation has been proposed, for example, in Japanese Unexamined Patent Application Publication No. 2004-008241.

Such living body tissue harvesting apparatus is composed of instruments such as a dissector, harvester, or the like. Through the dissector and harvester, an endoscope can be inserted, and an operator can harvest a blood vessel while watching the endoscopic image.

The dissector is an instrument which is inserted from a trocar that is a guide tube set to an incision part in the vicinity below a patient's knee, and by being inserted through the entire length of the blood vessel to be harvested, which gradually dissects the blood vessel and the peripheral tissues. The harvester is an instrument having a bipolar cutter for electrically cutting a side branch of the vessel dissected from the peripheral tissues by the dissector.

In the bipolar cutter of the harvester disclosed in Japanese Unexamined Patent Application Publication No. 2004-008241, a groove is provided at the tip portion thereof and a set of electrodes are arranged above and below the groove respectively. A side branch, which has gotten into the groove at the tip portion, may be cut due to the discharge that occurs between the two electrodes of the set while the blood stanching is ensured. In the bipolar cutter, the cutter body is formed of a synthetic resin such as polycarbonate that is a transparent member or ceramics.

SUMMARY OF THE INVENTION

The living body tissue harvesting apparatus of the present invention comprises a cutter body, an active electrode arranged on one side of the cutter body, a return electrode arranged on the other side of the cutter body, a heat-resistant member arranged in the cutter body between the active electrode and the return electrode, the heat-resistant member having a groove part that is formed such as to surround the tip part of the active electrode with which the living body tissue comes in contact.

DESCRIPTION OF THE PREFERRED EMBODIMENTS

First Embodiment

An embodiment of the invention will be described below with reference to FIG. 1 through FIG. 43.

Figure 1:
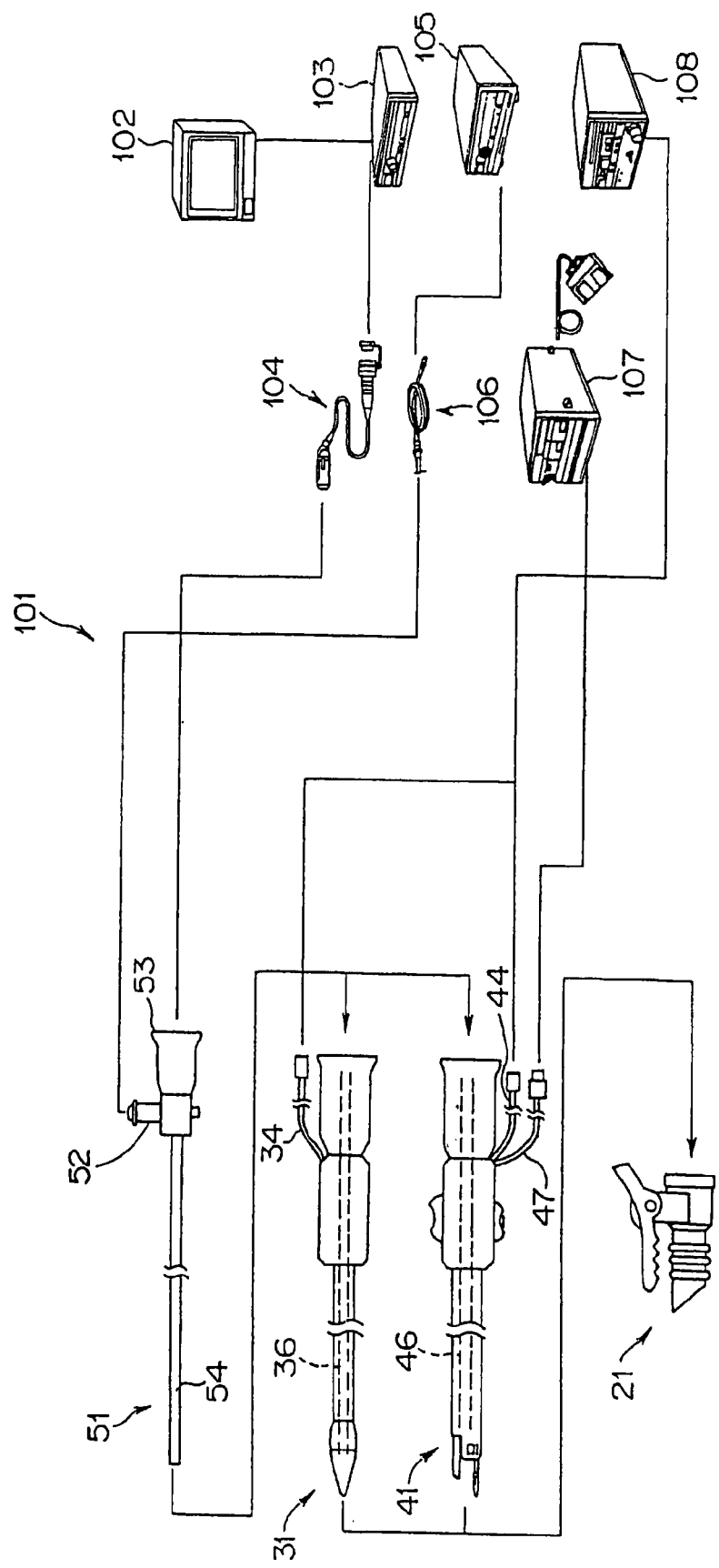
FIG. 1 is a structural view illustrating a structure of a surgery system according to a first embodiment of the present invention.
Figure 2:
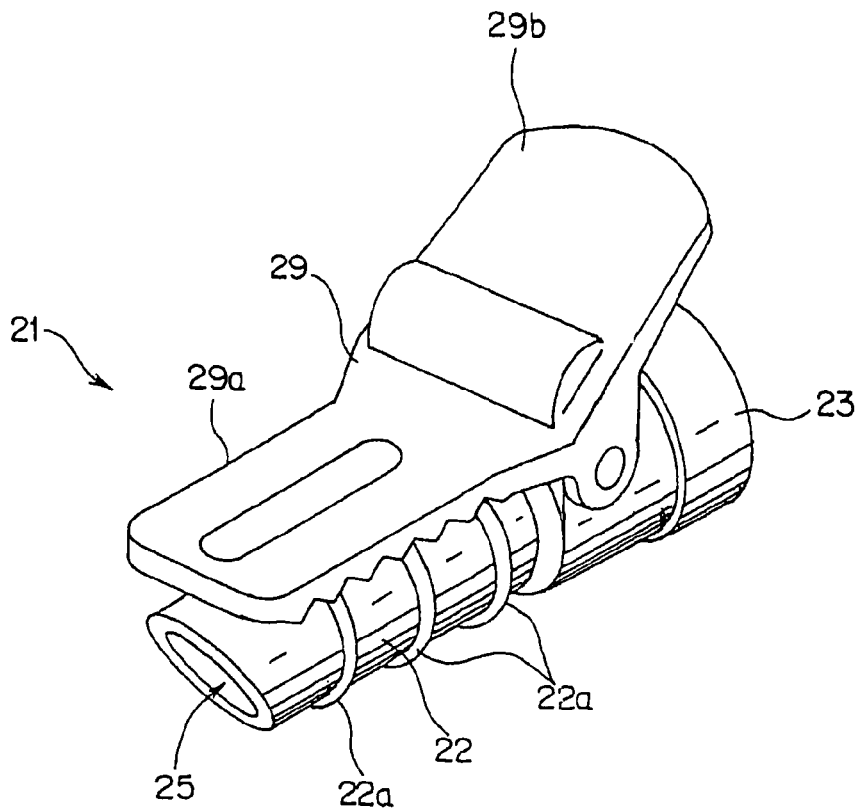
FIG. 2 is a perspective view illustrating a trocar according to the first embodiment of the present invention.
Figure 3:
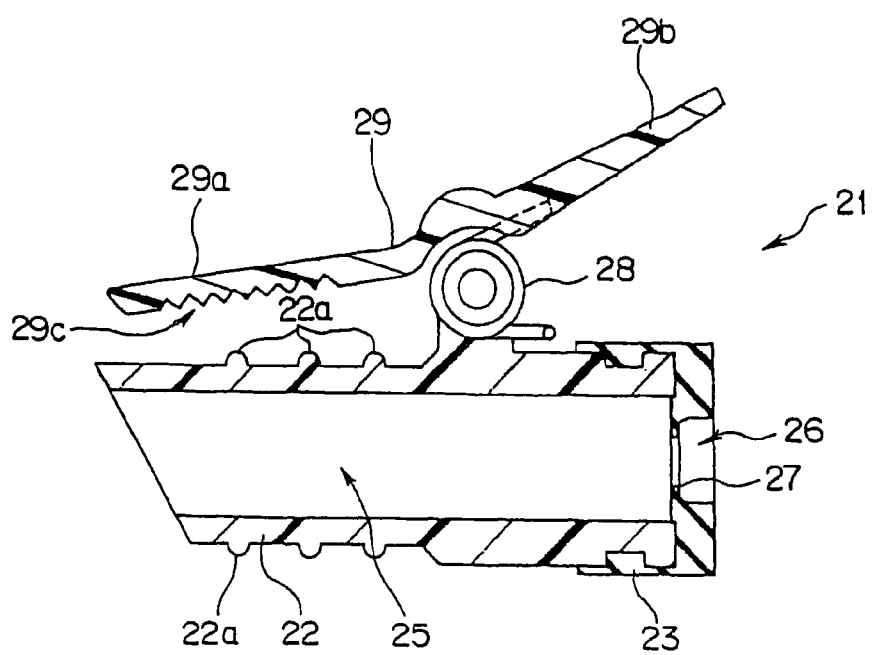
FIG. 3 is a longitudinal sectional view illustrating the trocar according to the first embodiment of the present invention.
Figure 4:
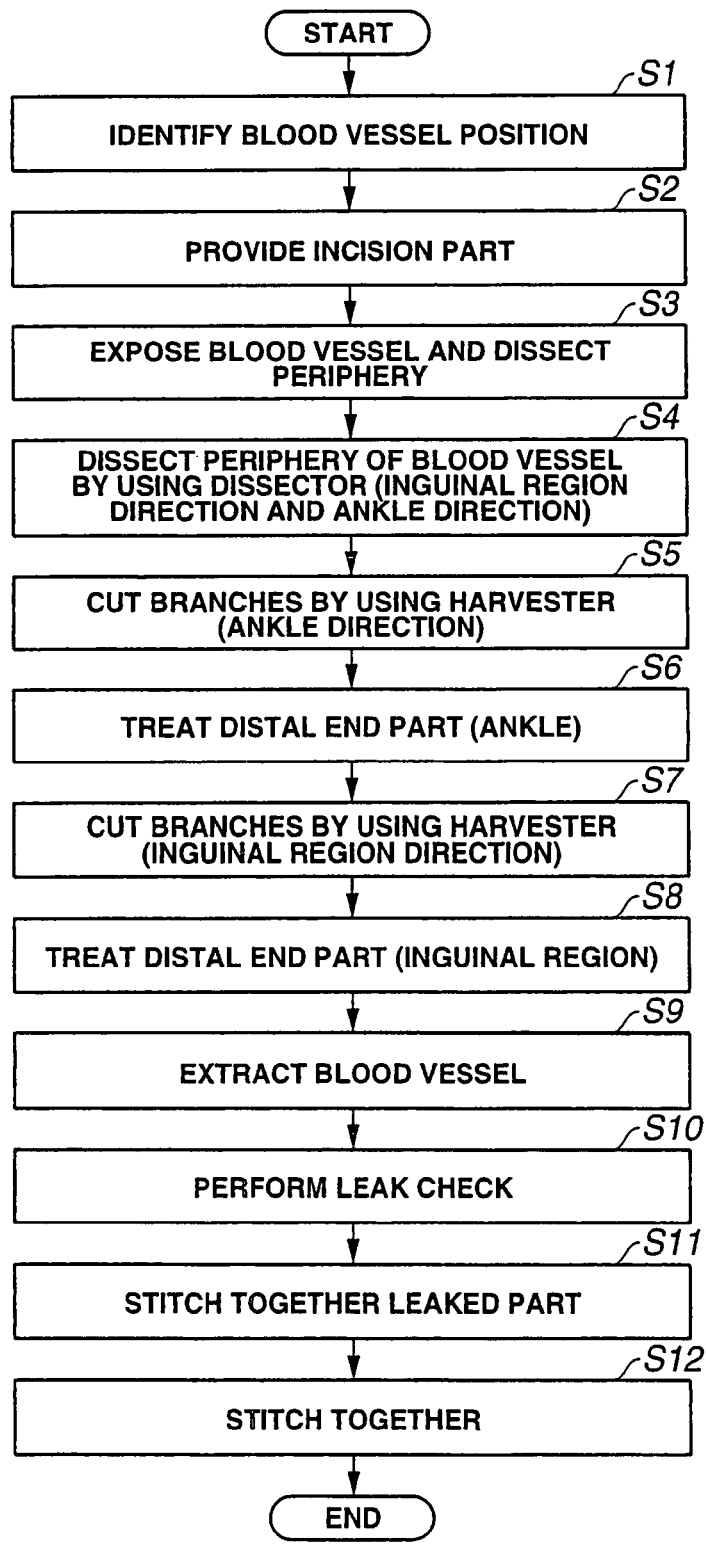
FIG. 4 is a flowchart for explaining an operating method of pulling a subcutaneous vessel and harvesting the pulled subcutaneous vessel.
Figure 5:
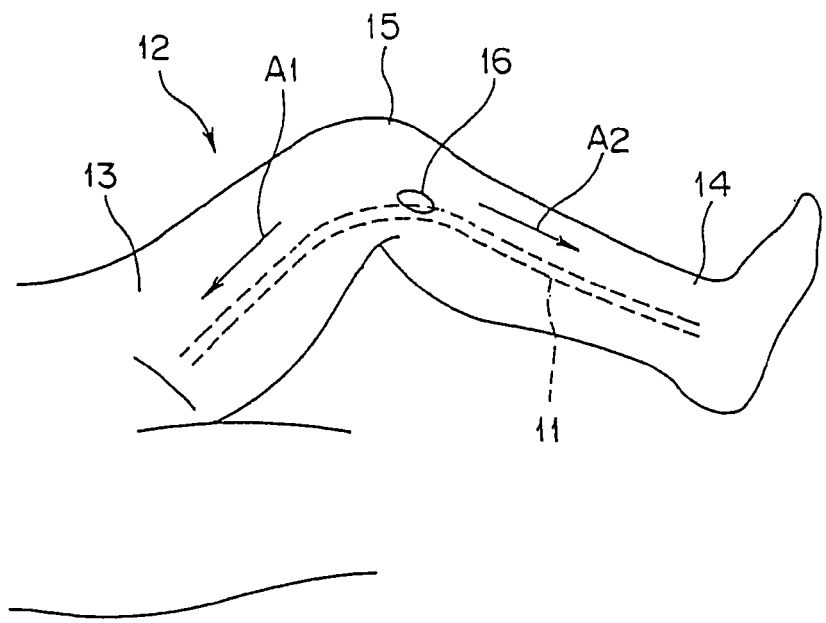
FIG. 5 is an illustration for explaining the operating method of pulling a subcutaneous vessel and harvesting the pulled subcutaneous vessel.
Figure 6:
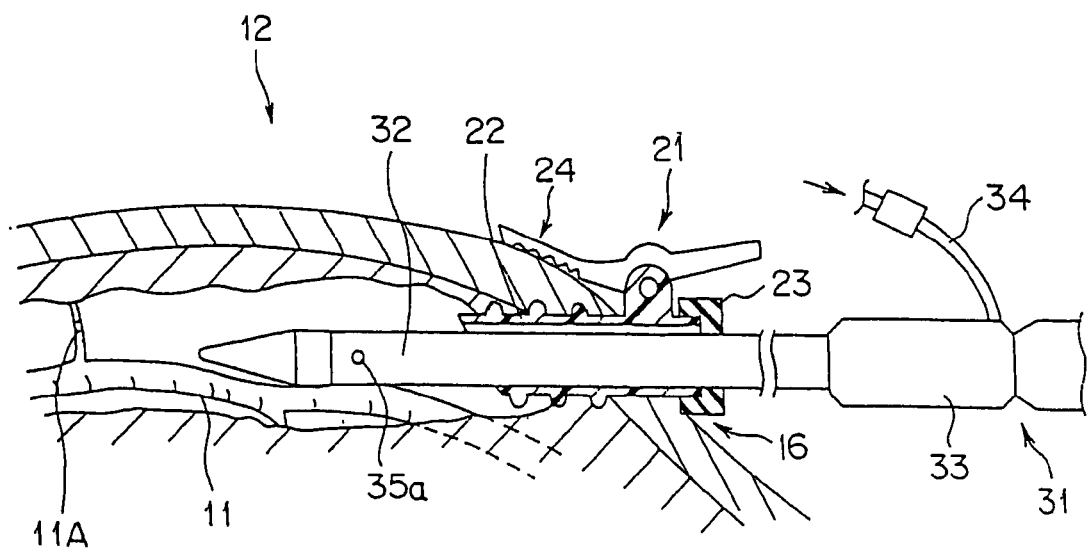
FIG. 6 is a cross-sectional view illustrating a state in which a dissector is inserted into subcutaneous of lower limb through a trocar according to the first embodiment of the present invention.
Figure 7:
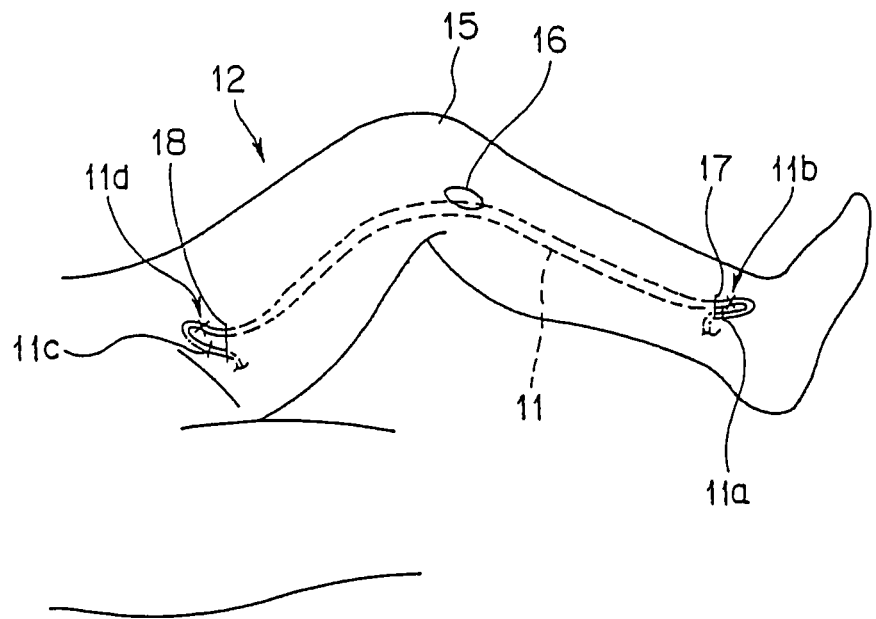
FIG. 7 is an illustration for explaining an operating method of pulling a subcutaneous vessel and harvesting the pulled subcutaneous vessel.
Figure 8:
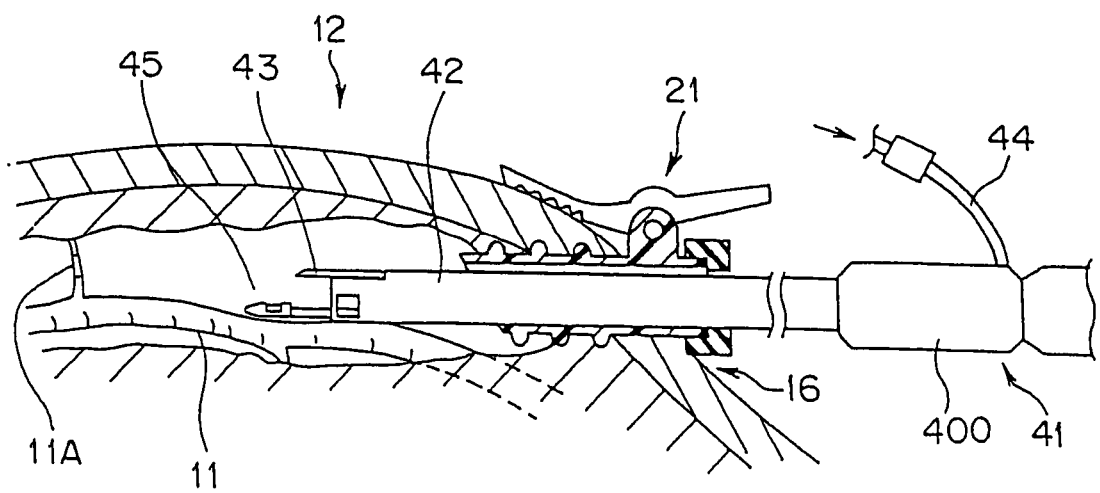
FIG. 8 is a cross-sectional view illustrating a state in which a harvester is inserted into subcutaneous of lower limb from an incision part through the trocar.
Figure 9:
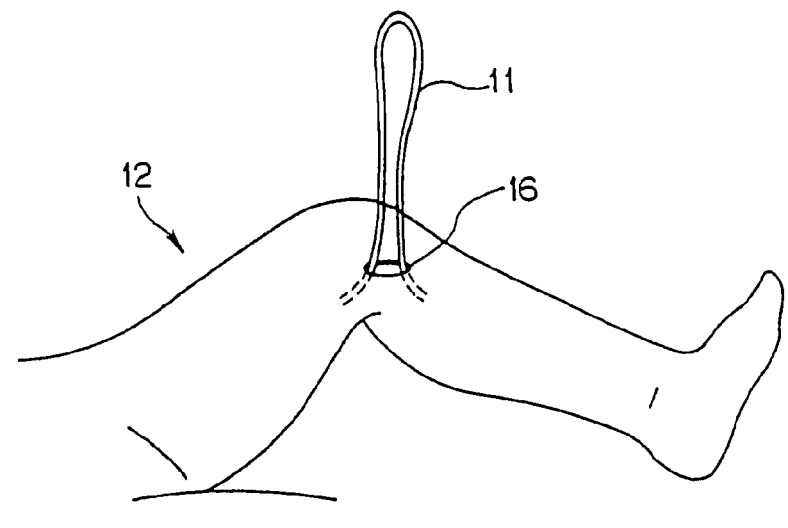
FIG. 9 is an illustration for explaining an operating method of pulling a subcutaneous vessel and harvesting the pulled subcutaneous vessel.
Figure 10:
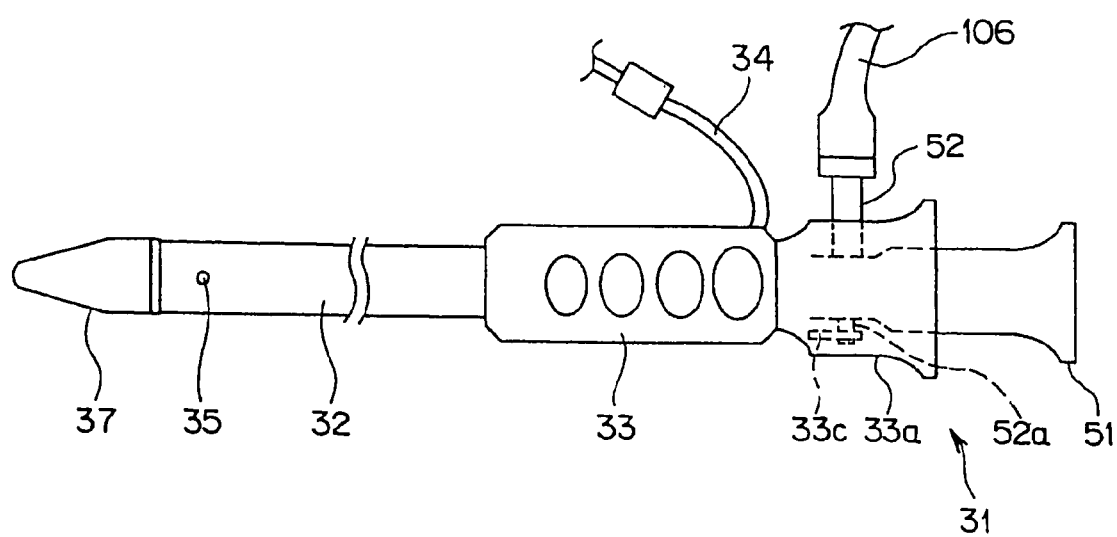
FIG. 10 is a side view of the dissector according to the first embodiment of the present invention.
Figure 11:
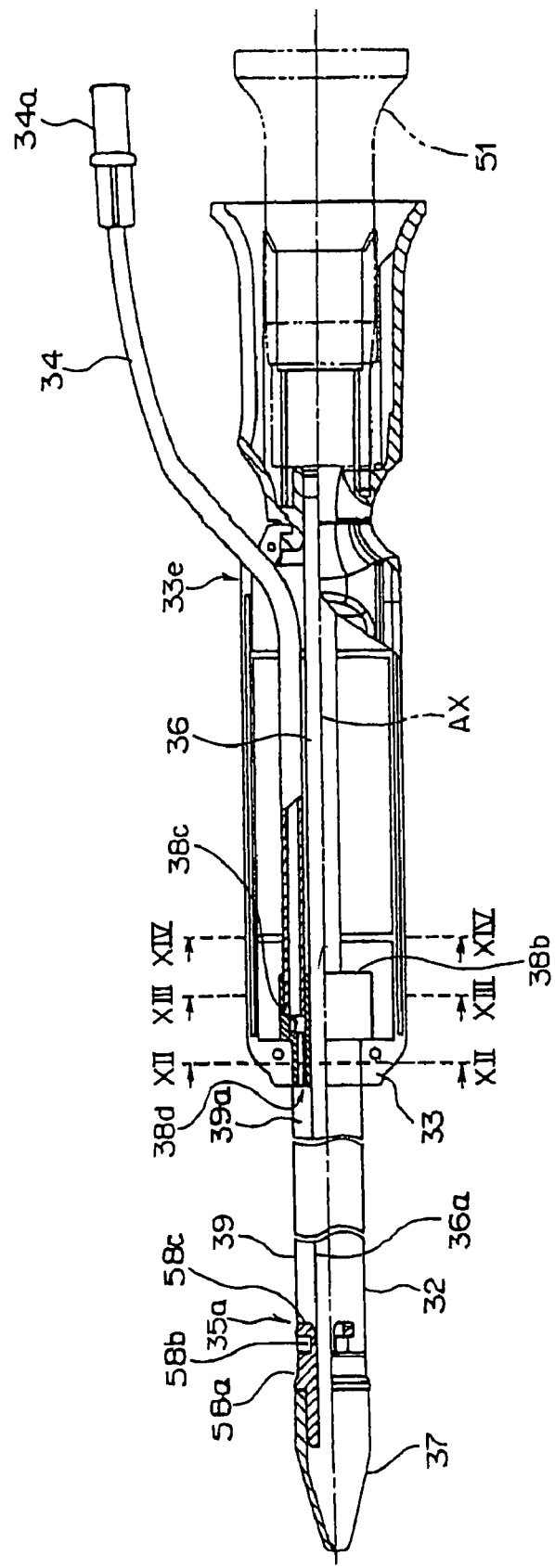
FIG. 11 is a partial cross-sectional view of the dissector according to the first embodiment of the present invention.
Figure 12:
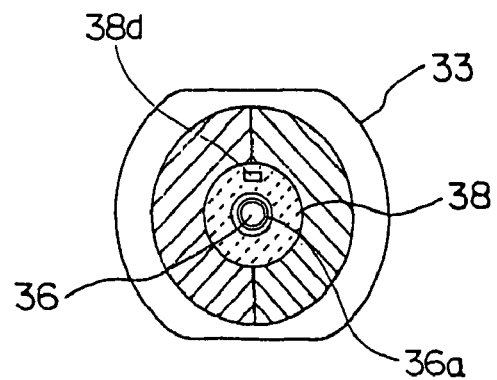
FIG. 12 is a cross-sectional view taken along the line XII-line XII of FIG. 11 according to the first embodiment of the present invention.
Figure 13:
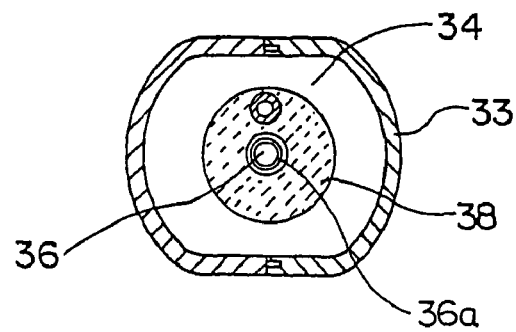
FIG. 13 is a cross-sectional view taken along the line XIII-line XIII of FIG. 11 according to the first embodiment of the present invention.
Figure 14:
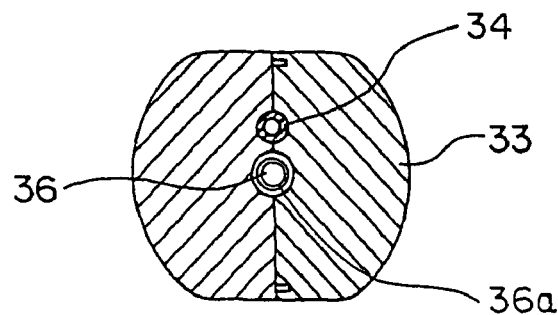
FIG. 14 is a cross-sectional view taken along the line XIV-line XIV of FIG. 11 according to the first embodiment of the present invention.
Figure 15:
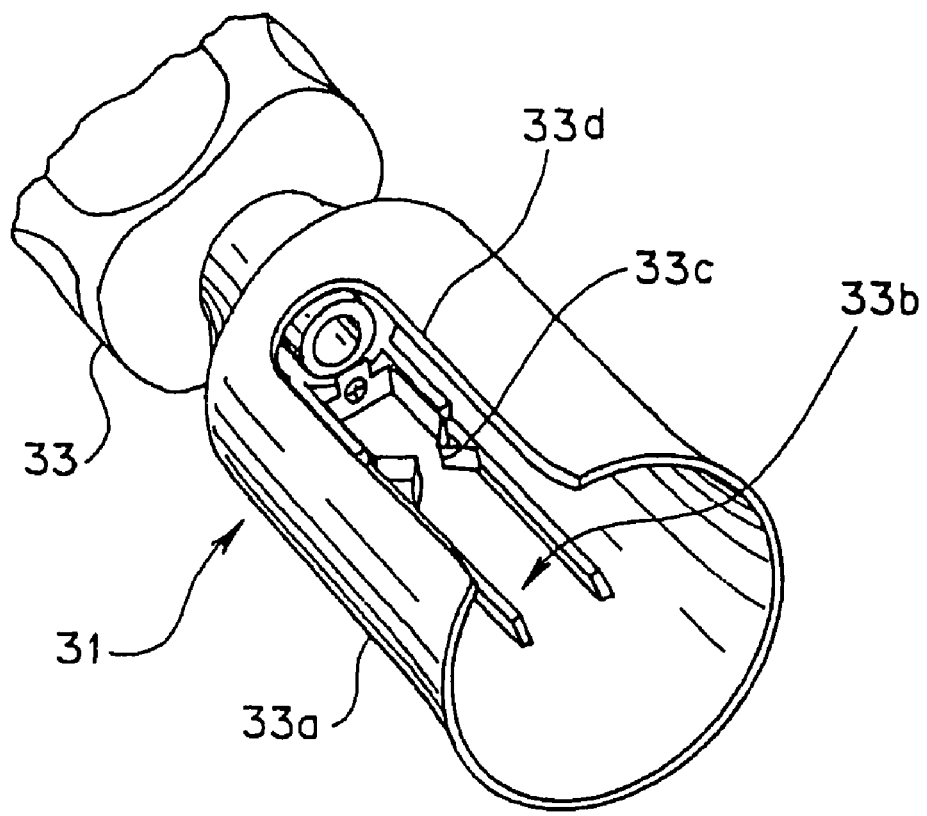
FIG. 15 is a partial perspective view of the base end side of the dissector according to the first embodiment of the present invention.
Figure 16:
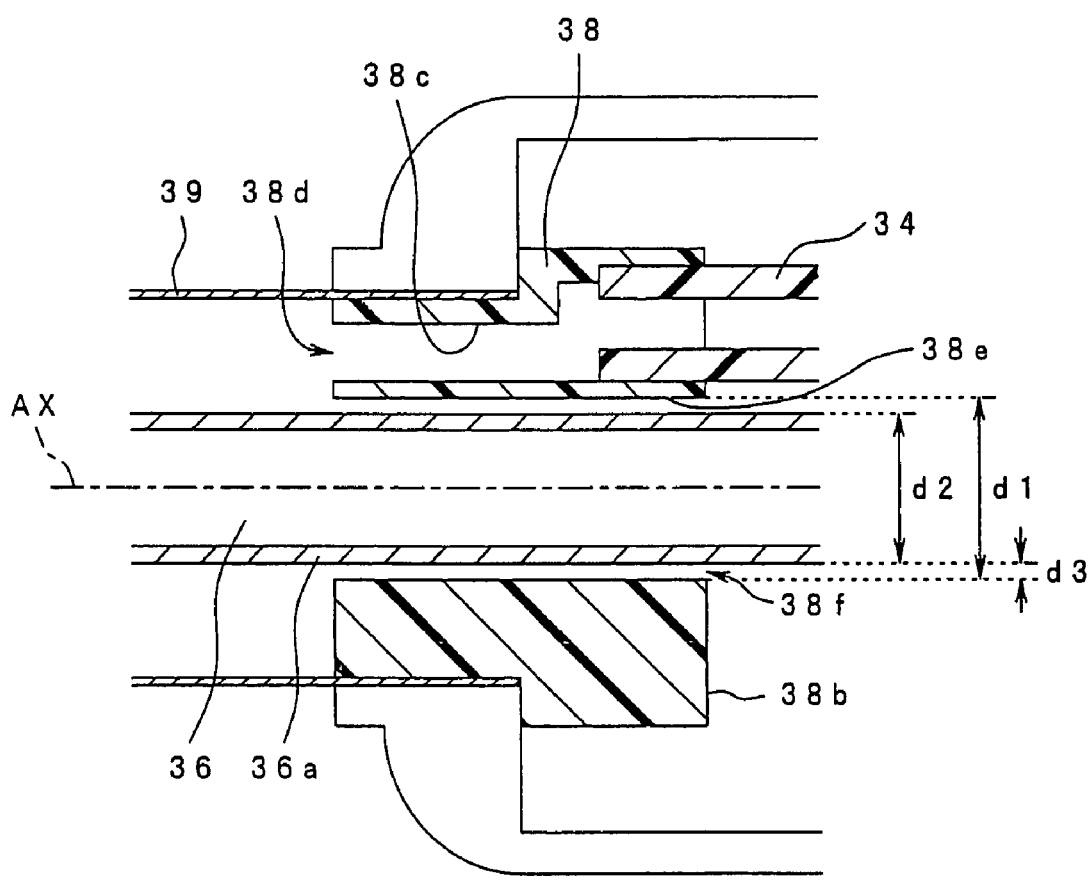
FIG. 16 is a partial cross-sectional view of the tip side of a grip section according to the first embodiment of the present invention.
Figure 17:
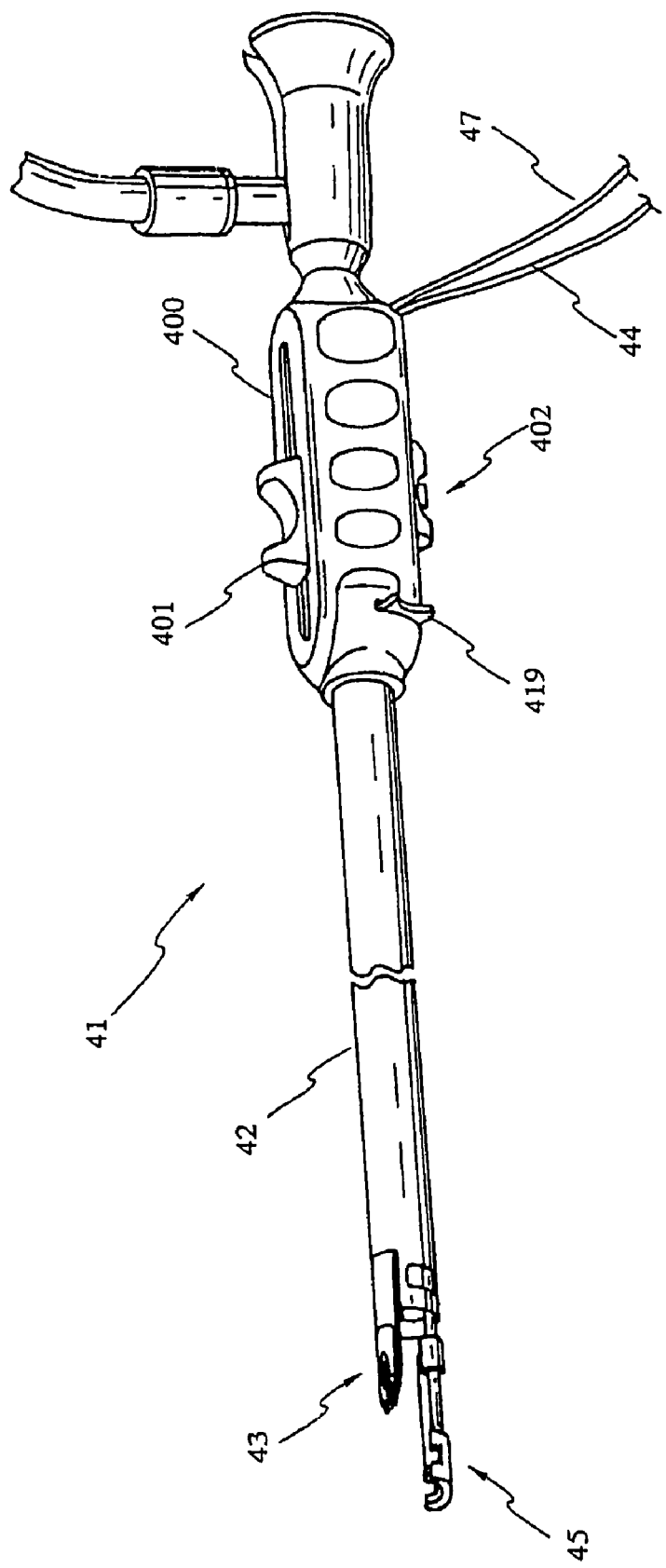
FIG. 17 is a perspective view of a harvester according to the first embodiment of the present invention.
Figure 18:
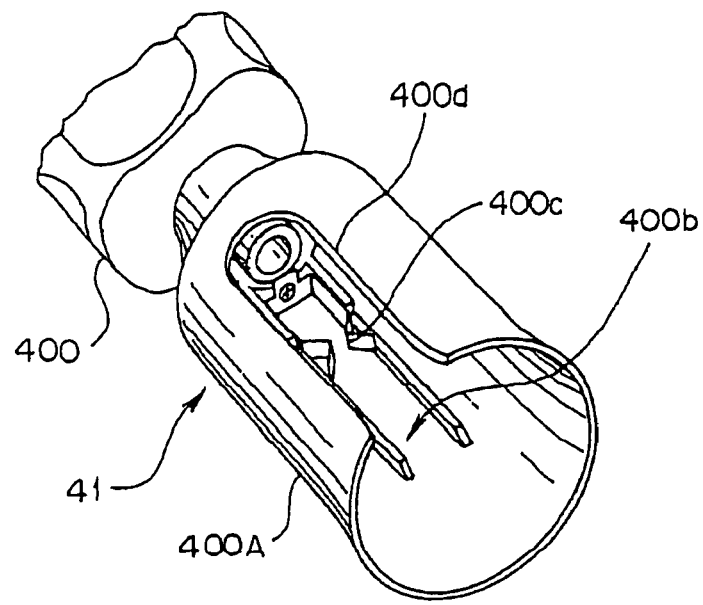
FIG. 18 is a partial perspective view for explaining a structure of the base end side of the harvester according to the first embodiment of the present invention.
Figure 19:
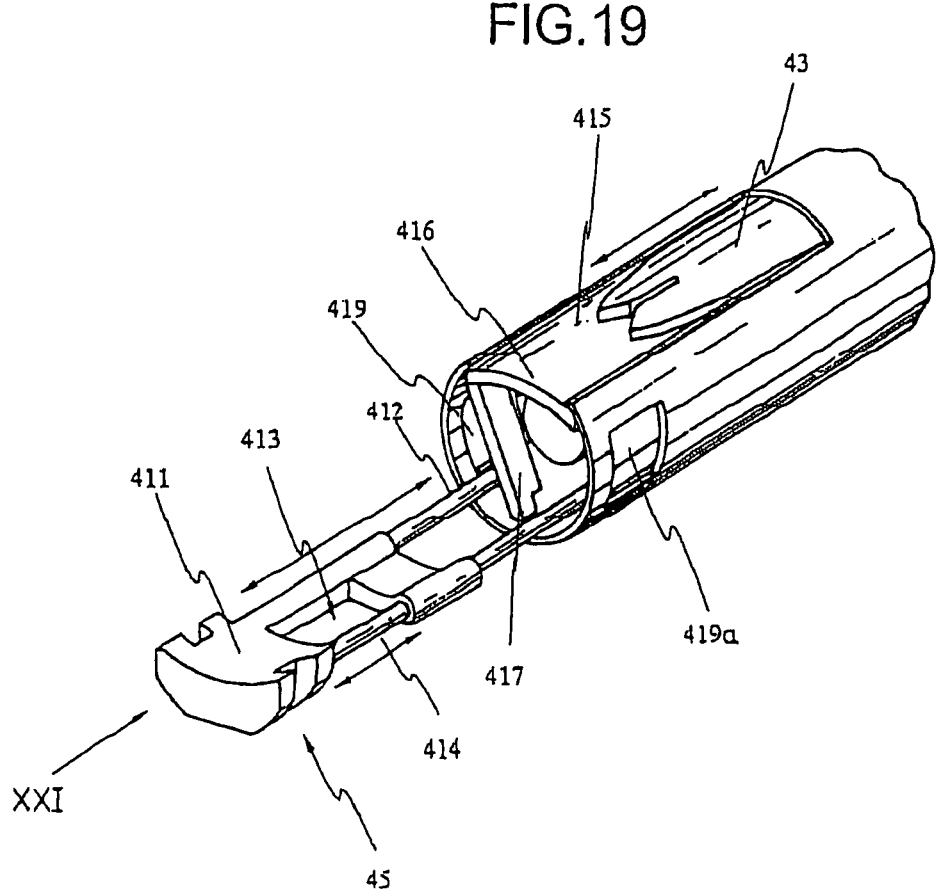
FIG. 19 is a partial perspective view showing a structure of the tip side of the harvester according to the first embodiment of the present invention.
Figure 20:
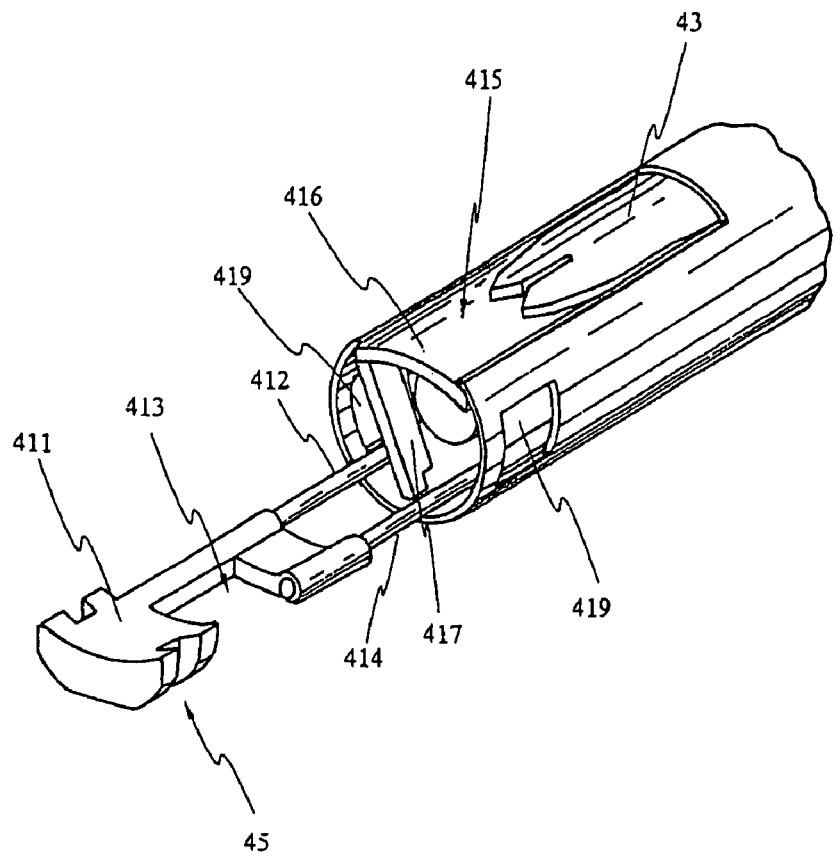
FIG. 20 is an illustration for explaining operation of a lock axis of FIG. 19.
Figure 21:
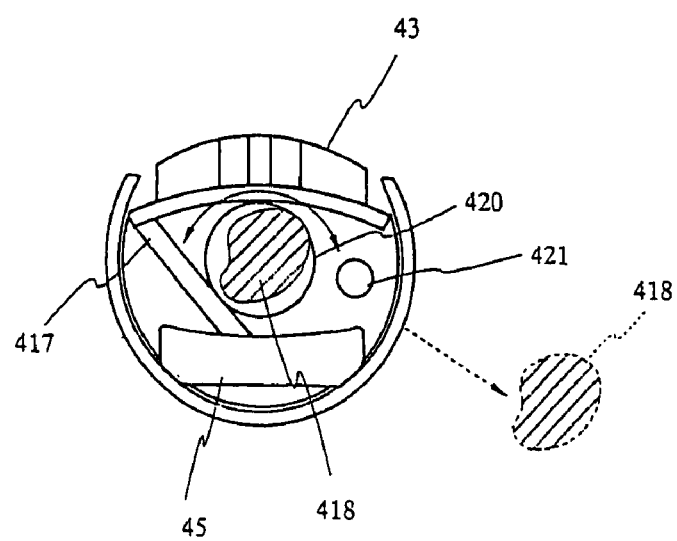
FIG. 21 is an illustration viewed from the direction of the arrow XXI of FIG. 19.
Figure 22:
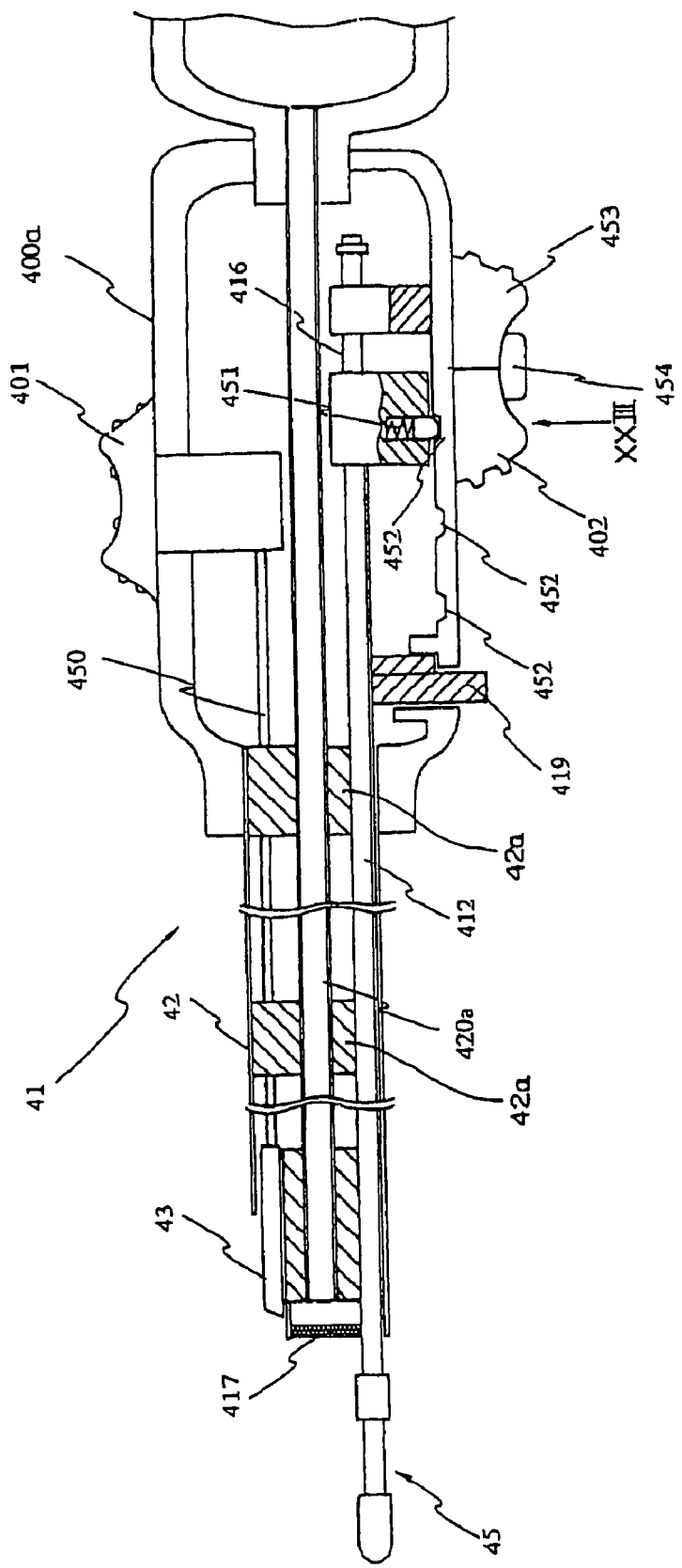
FIG. 22 is a cross-sectional view in the direction of the long axis illustrating an operating structure of the harvester according to the first embodiment of the present invention.
Figure 23:
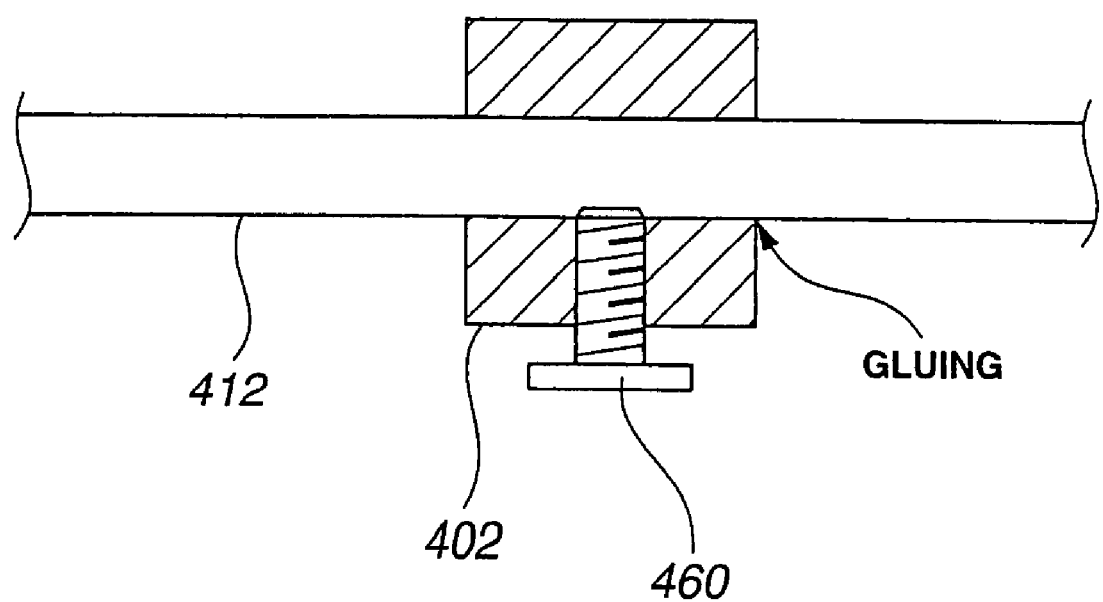
FIG. 23 is a conceptual view of an attachment of a vein keeper lever viewed from the direction of the arrow XXIII of FIG. 22.
Figure 24:
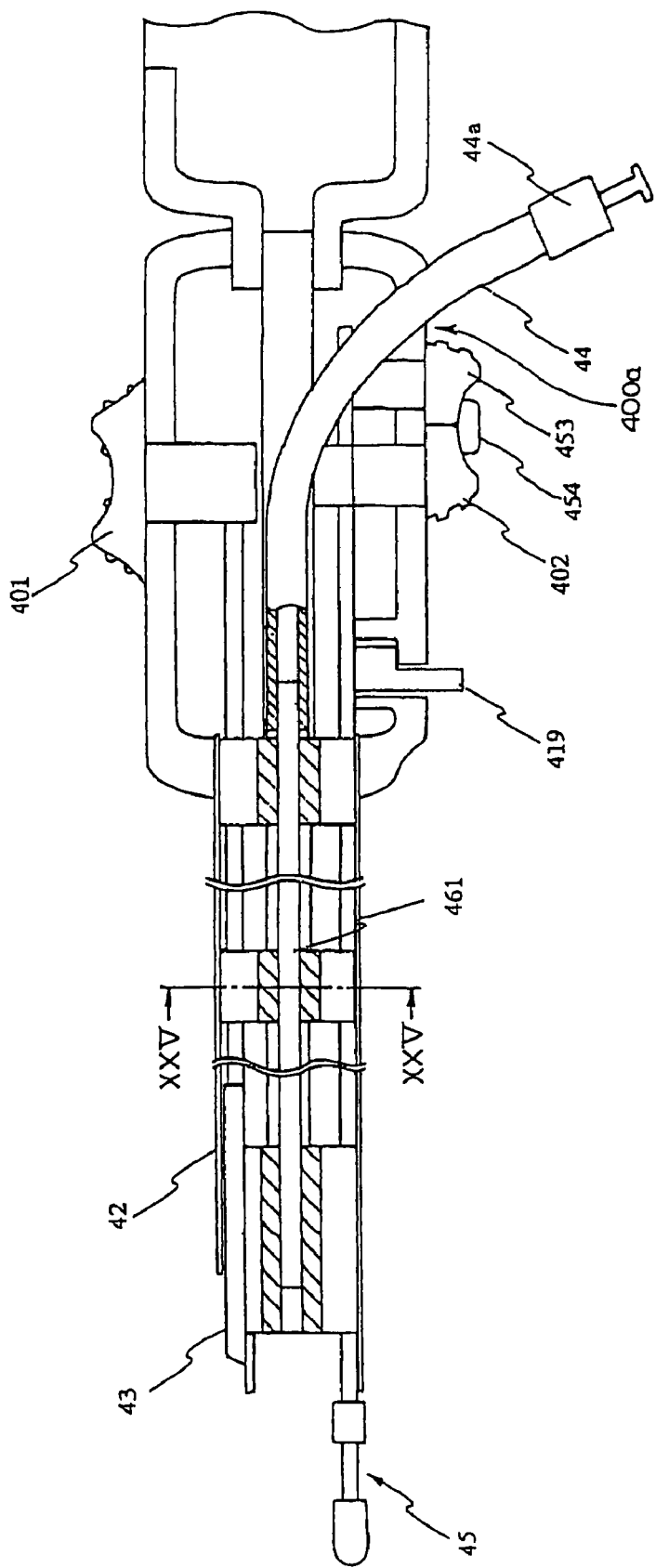
FIG. 24 is a cross-sectional view in the direction of the long axis illustrating a structure for supplying gas of the harvester according to the first embodiment of the present invention.
Figure 25:
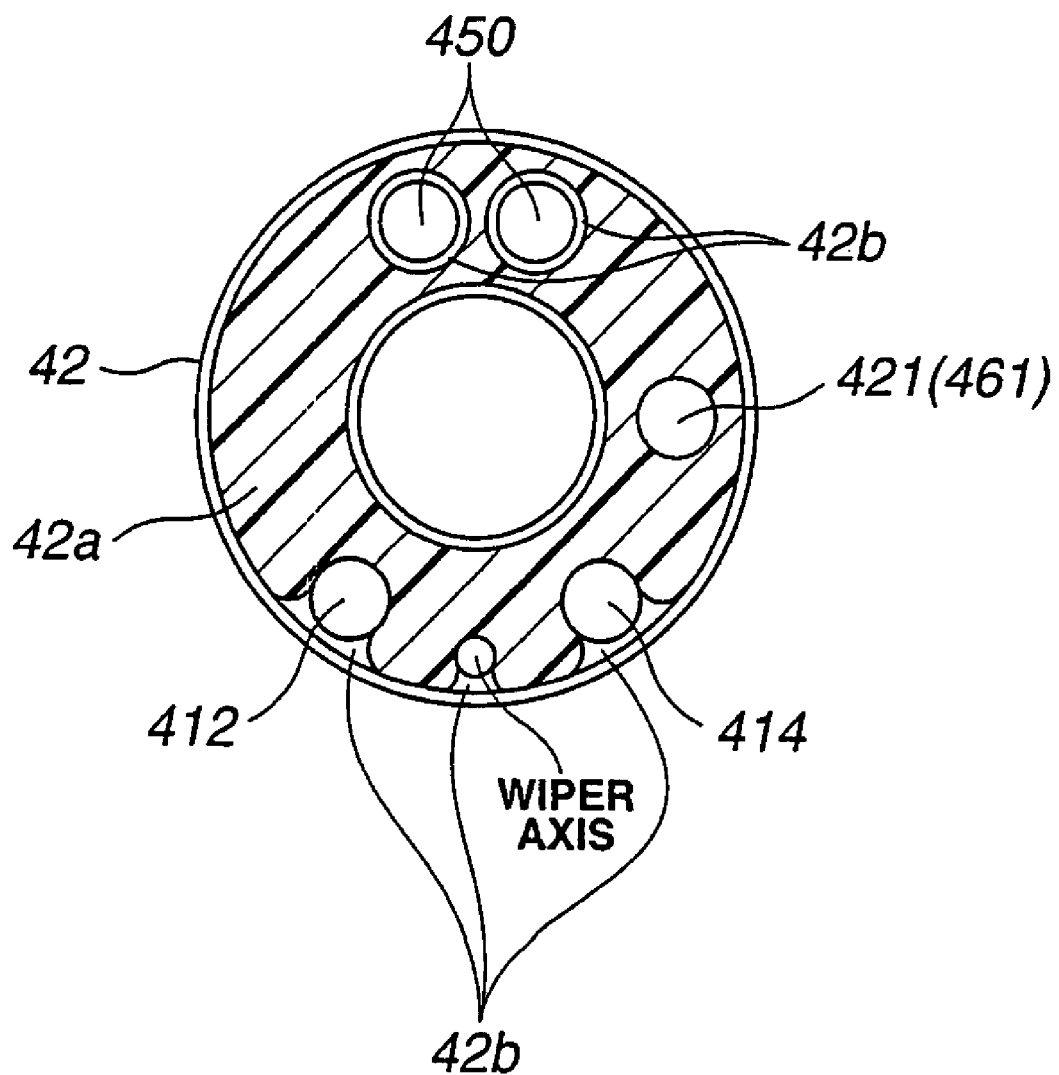
FIG. 25 is a cross-sectional view taken along the line XXV-line XXV of FIG. 24.
Figure 26:
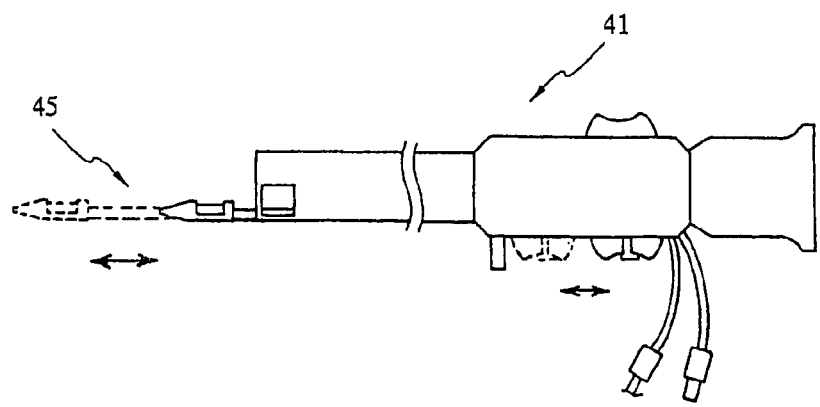
FIG. 26 is a first illustration for explaining operation of a vein keeper of the harvester according to the first embodiment of the present invention.
Figure 27:
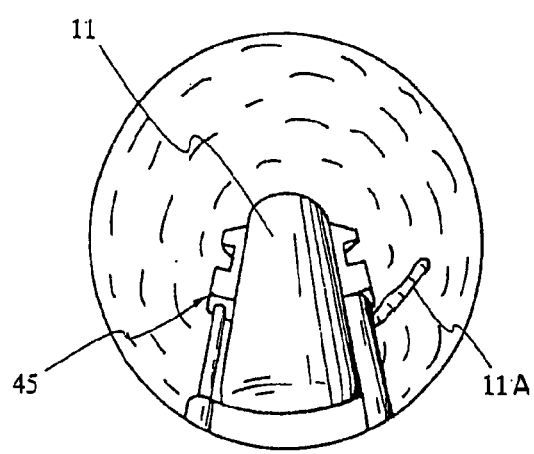
FIG. 27 is a second illustration for explaining operation of the vein keeper of the harvester according to the first embodiment of the present invention.
Figure 28:
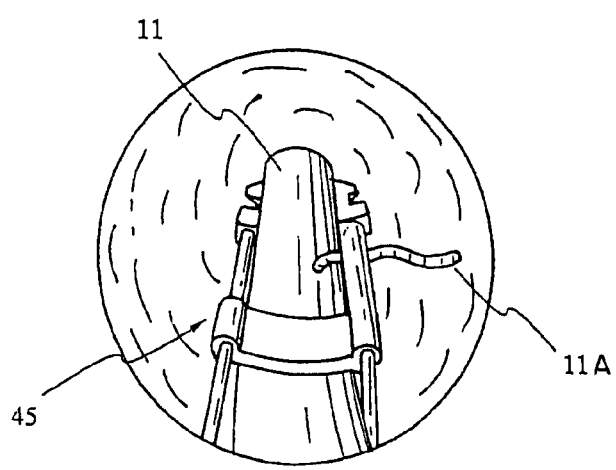
FIG. 28 is a third illustration for explaining operation of the vein keeper of the harvester according to the first embodiment of the present invention.
Figure 29:
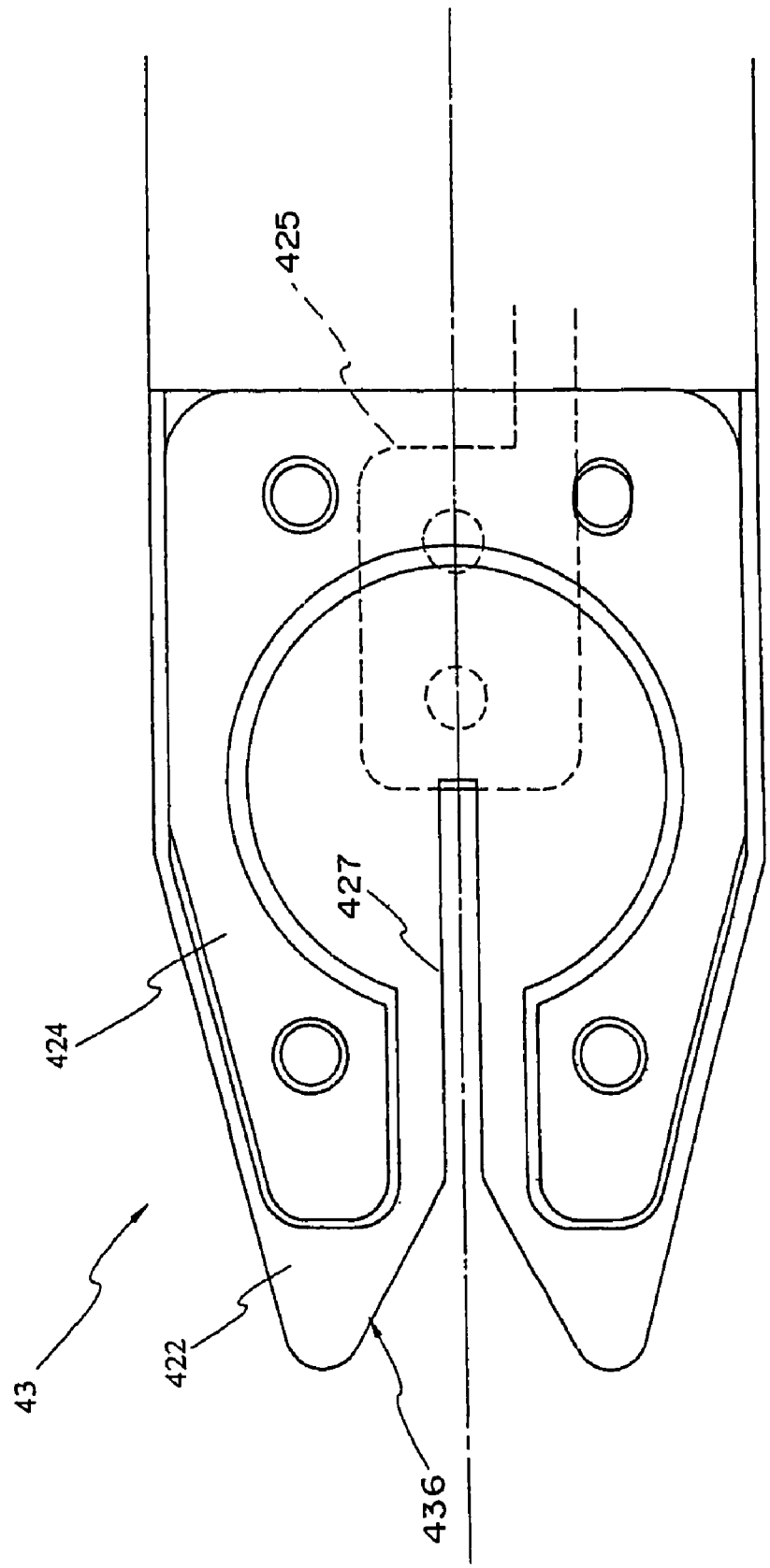
FIG. 29 is an illustration of a bipolar cutter viewed from the top surface of the tip part of the bipolar cutter according to the first embodiment of the present invention.
Figure 30:
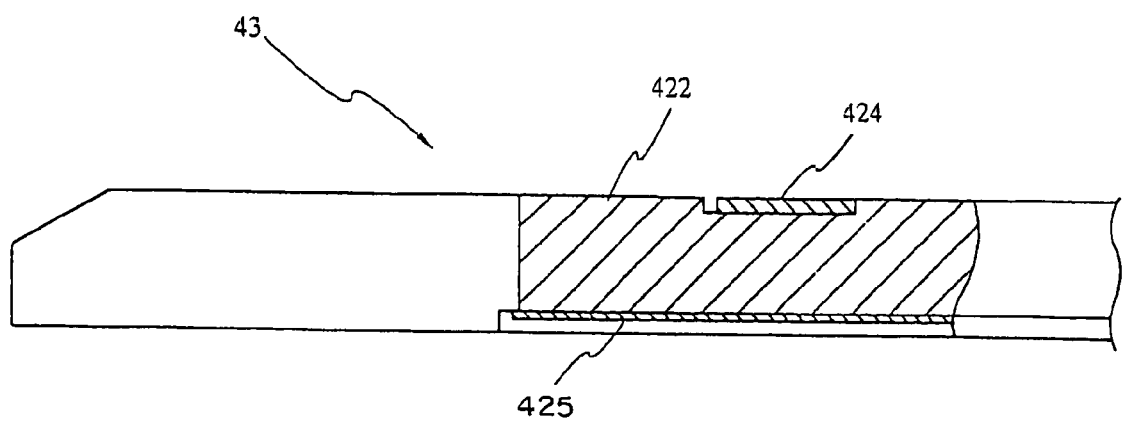
FIG. 30 is a cross-sectional view of the bipolar cutter of FIG. 29.
Figure 31:
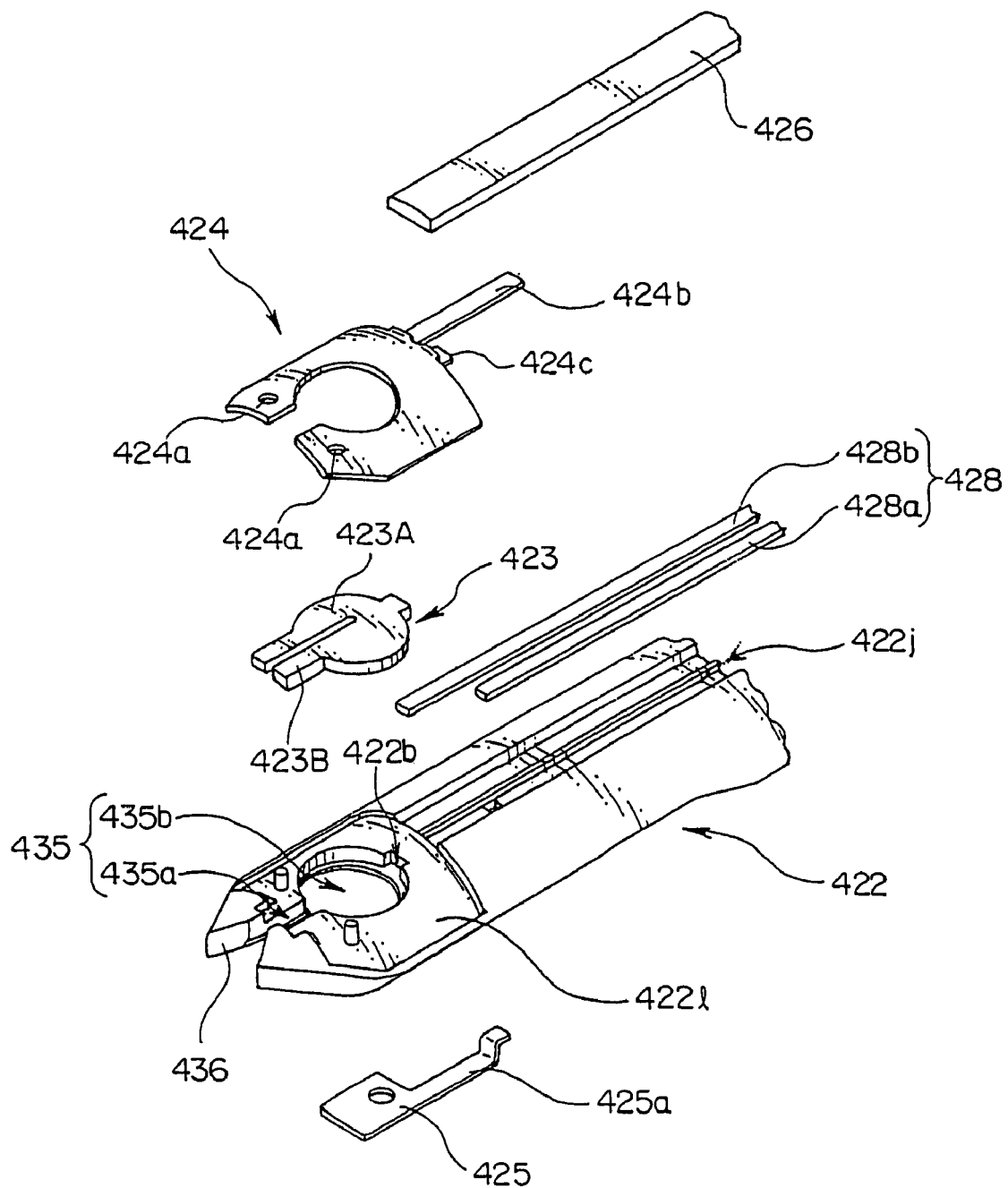
FIG. 31 is an exploded perspective view of a tip part of a modified bipolar cutter.
Figure 32:
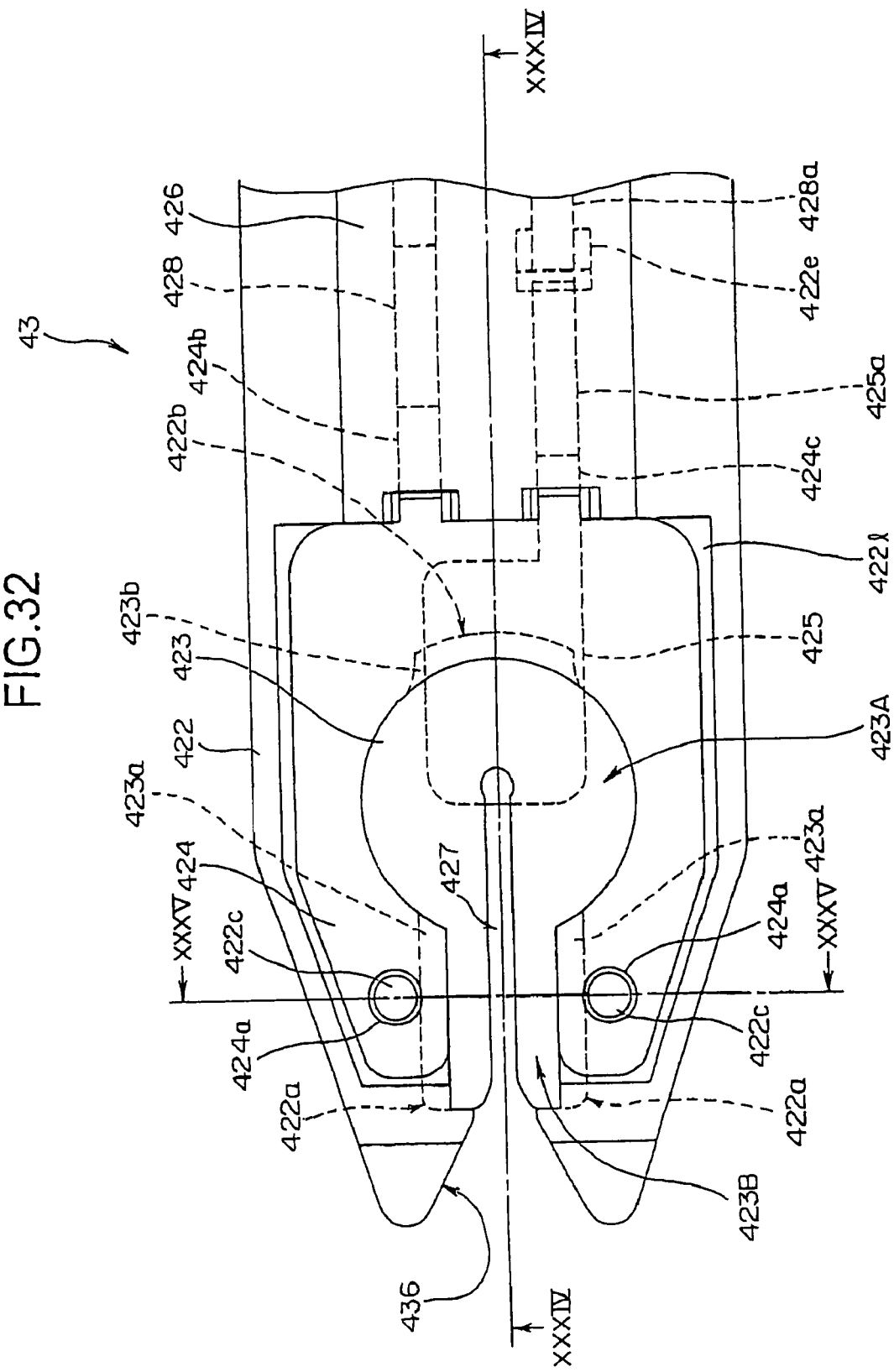
FIG. 32 is an illustration of the bipolar cutter viewed from the top surface according to the first embodiment of the present invention.
Figure 33:
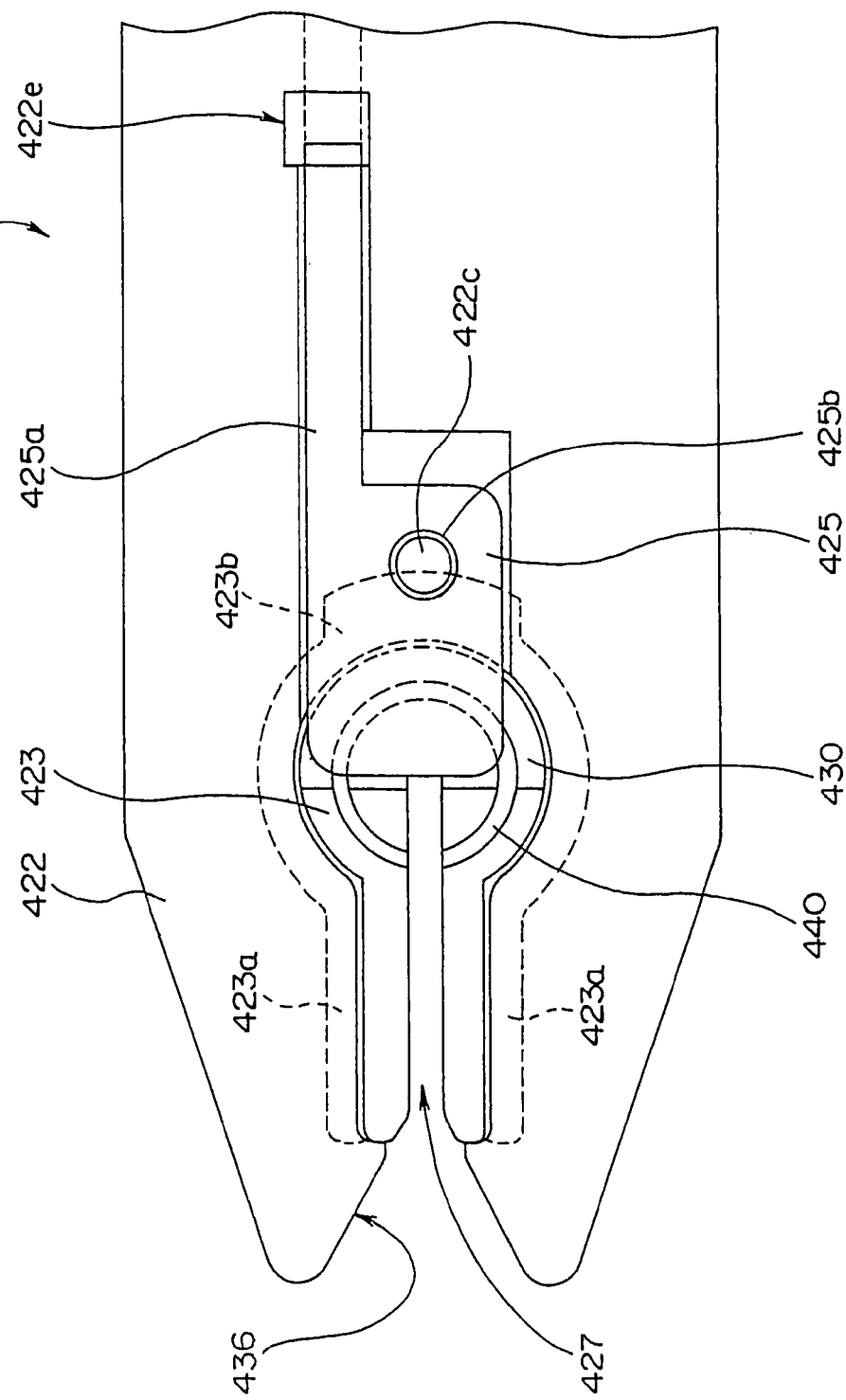
FIG. 33 is an illustration of the bipolar cutter viewed from the under surface according to the first embodiment of the present invention.
Figure 34:
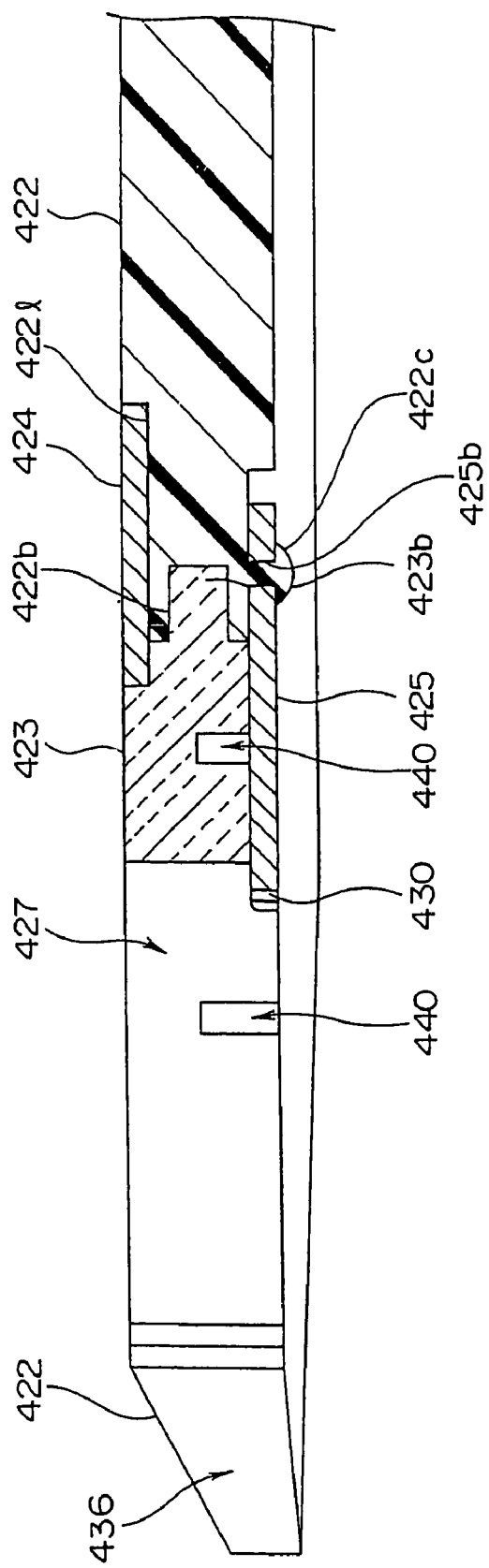
FIG. 34 is a cross-sectional view of the bipolar cutter taken along the line XXXIV-line XXXIV of FIG. 32.
Figure 35:
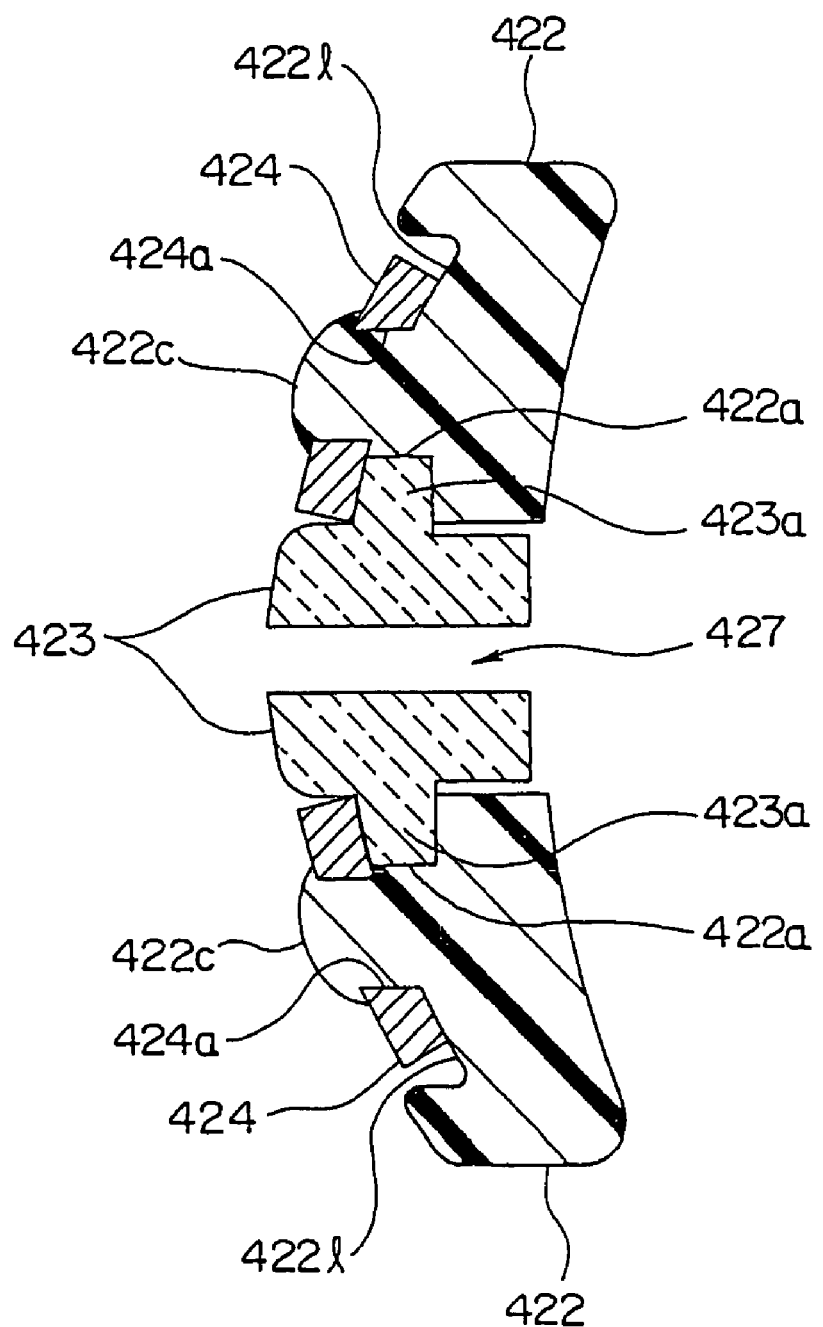
FIG. 35 is a cross-sectional view of the bipolar cutter taken along the line XXXV-line XXXV of FIG. 32.
Figure 36:
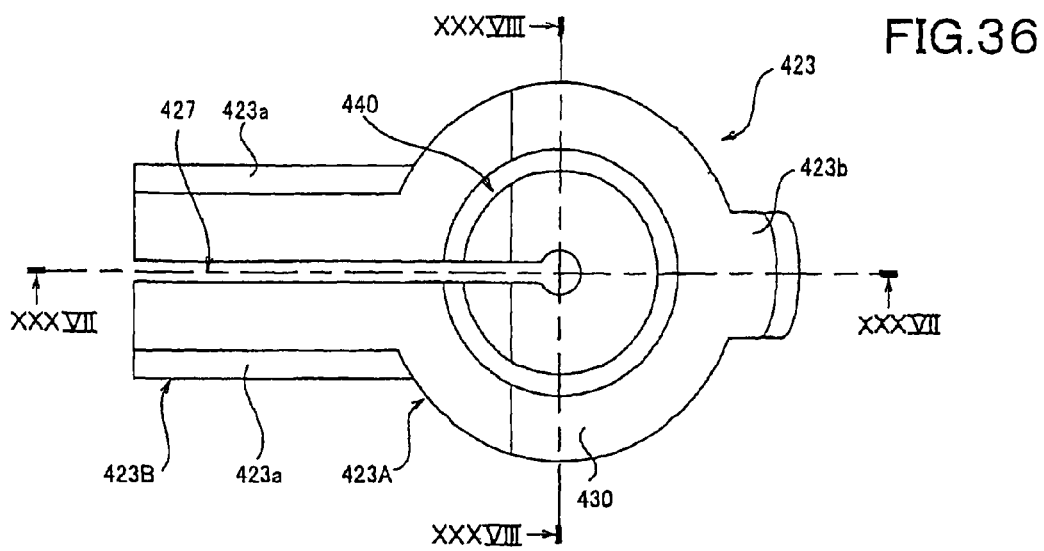
FIG. 36 is an illustration of a tissue holding part viewed from the under surface according to the first embodiment of the present invention.
Figure 37:
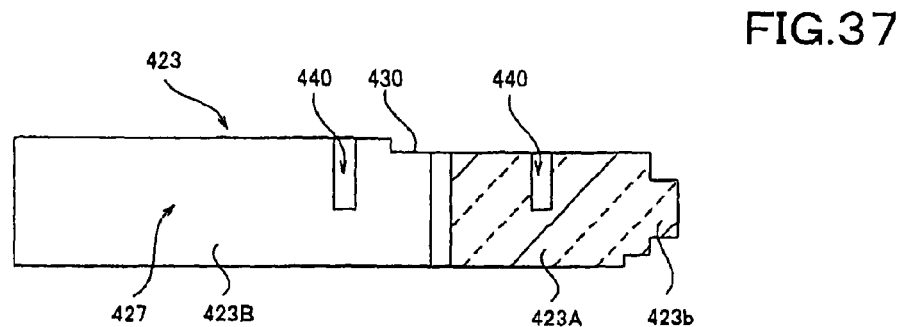
FIG. 37 is a cross-sectional view of the tissue holding part taken along the line XXXVII-line XXXVII of FIG. 36 according to the first embodiment of the present invention.
Figure 38:
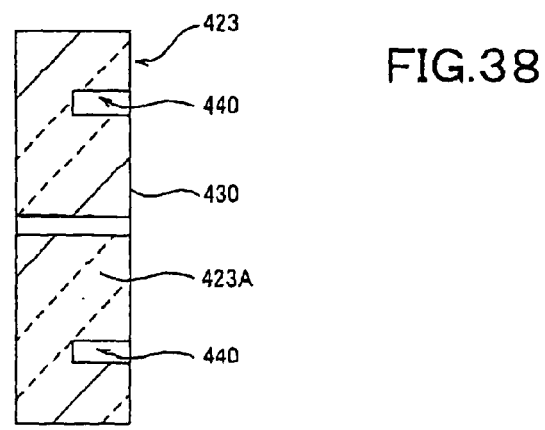
FIG. 38 is a cross-sectional view of the tissue holding part taken along the line XXXVIII-line XXXVIII of FIG. 36 according to the first embodiment of the present invention.
Figure 39:
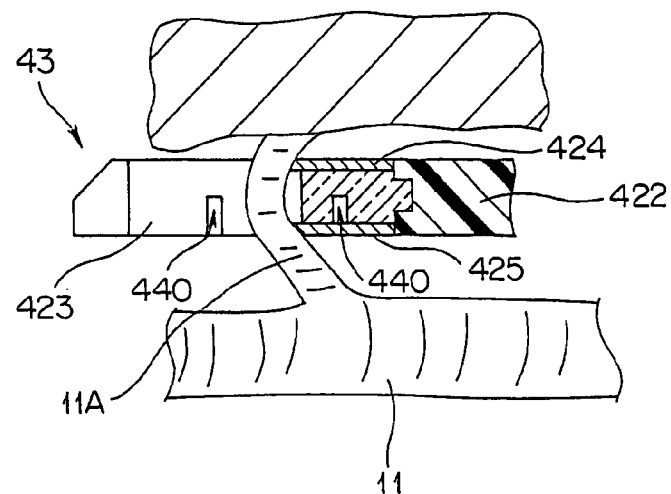
FIG. 39 is an illustration for explaining cutting operation of a branch with the bipolar cutter according to the first embodiment of the present invention.
Figure 40:
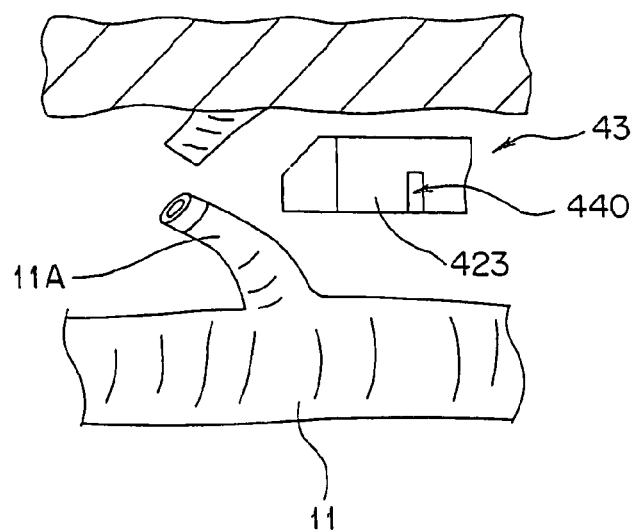
FIG. 40 is an illustration for explaining the cutting operation of the branch with the bipolar cutter according to the first embodiment of the present invention.
Figure 41:
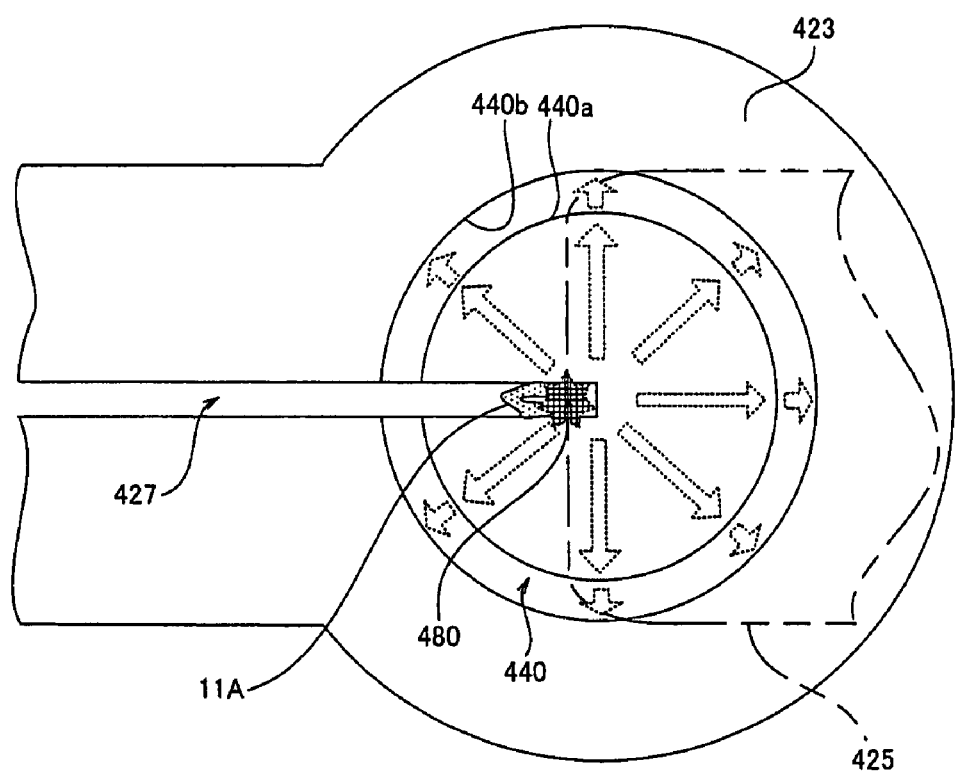
FIG. 41 illustrates the tissue holding part viewed from the under surface at a time of cutting the branch.
Figure 42:
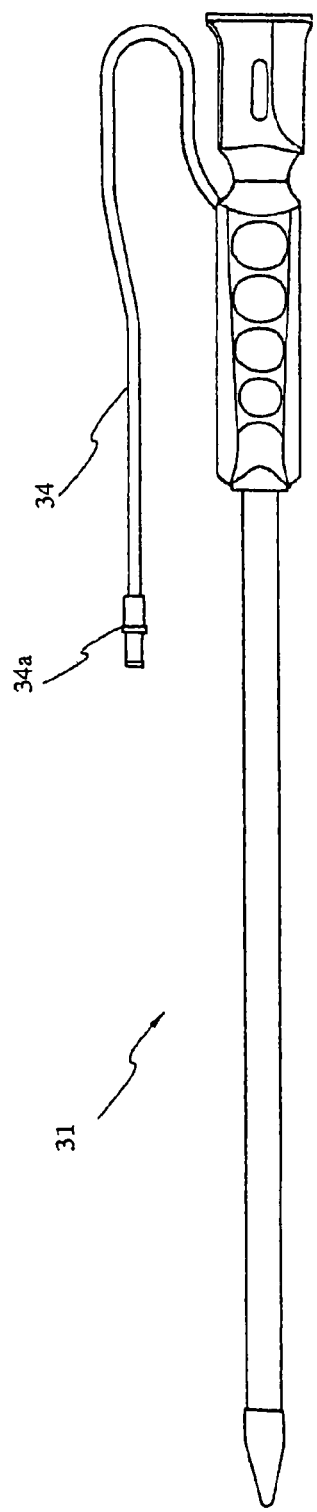
FIG. 42 illustrates an external appearance of a disposable dissector according to the first embodiment of the present invention.
Figure 43:
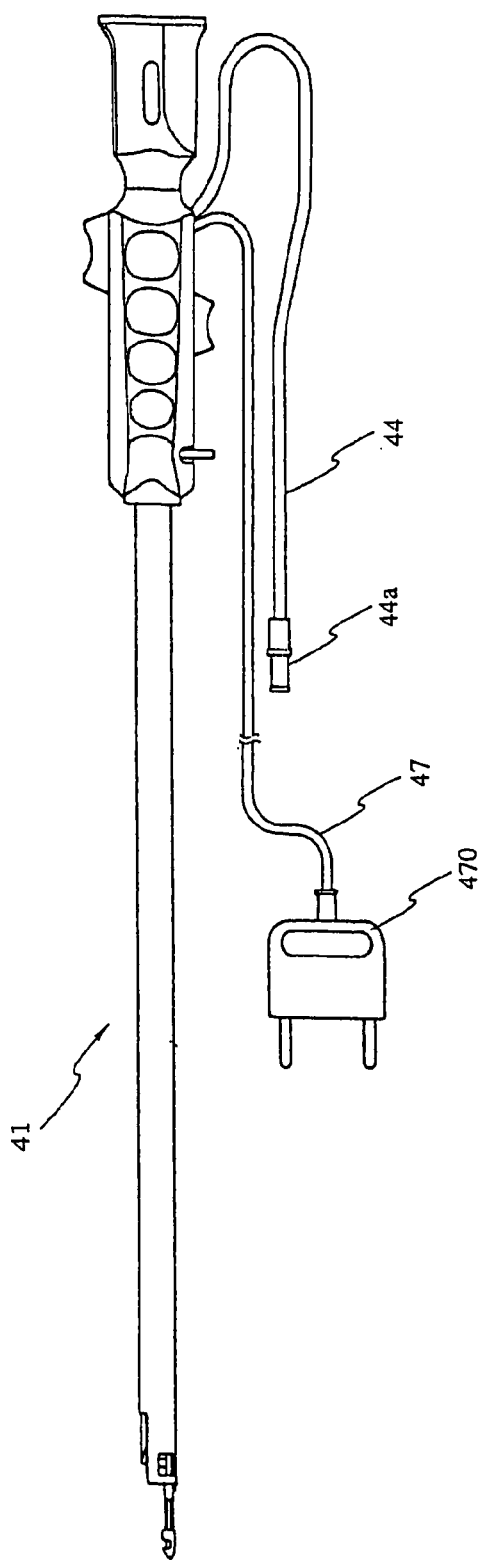
FIG. 43 illustrates an external appearance of a disposable harvester according to the first embodiment of the present invention.

FIG. 1 through FIG. 43 relate to a surgery system in which a subcutaneous vessel is pulled and harvested according to the embodiment of the present invention. FIG. 1 is a structural view illustrating a structure of a surgery system. FIG. 2 is a perspective view illustrating a trocar. FIG. 3 is a longitudinal sectional view illustrating the trocar. FIG. 4 is a flowchart for explaining an operating method of pulling a subcutaneous vessel and harvesting the pulled subcutaneous vessel. FIG. 5 is an illustration for explaining the operating method of pulling a subcutaneous vessel and harvesting the pulled subcutaneous vessel. FIG. 6 is a cross-sectional view illustrating a state in which a dissector is inserted into subcutaneous of lower limb through a trocar. FIG. 7 is an illustration for explaining an operating method of pulling a subcutaneous vessel and harvesting the pulled subcutaneous vessel. FIG. 8 is a cross-sectional view illustrating a state in which a harvester is inserted into subcutaneous of lower limb from an incision part through the trocar. FIG. 9 is an illustration for explaining an operating method of pulling a subcutaneous vessel and harvesting the pulled subcutaneous vessel. FIG. 10 is a side view of the dissector. FIG. 11 is a partial cross-sectional view of the dissector. FIG. 12 is a cross-sectional view taken along the line XII-line XII of FIG. 11. FIG. 13 is a cross-sectional view taken along the line XIII-line XIII of FIG. 11. FIG. 14 is a cross-sectional view taken along the line XIV-line XIV of FIG. 11. FIG. 15 is a partial perspective view of the base end side of the dissector. FIG. 16 is a partial cross-sectional view of the tip side of a grip section. FIG. 17 is a perspective view of a harvester. FIG. 18 is a partial perspective view for explaining a structure of the base end side of the harvester. FIG. 19 is a partial perspective view showing a structure of the tip side of the harvester. FIG. 20 is an illustration for explaining operation of a lock axis shown of 19. FIG. 21 is an illustration viewed from the direction of the arrow XXI in FIG. 19. FIG. 22 is a cross-sectional view in the direction of the long axis illustrating an operating structure of the harvester. FIG. 23 is a conceptual view of an attachment of a vein keeper lever viewed from the direction of the arrow XXIII of FIG. 22. FIG. 24 is a cross-sectional view in the direction of the long axis illustrating a structure for supplying gas of the harvester. FIG. 25 is a cross-sectional view taken along the line XXV-line XXV of FIG. 24. FIG. 26 is a first illustration for explaining operation of a vein keeper. FIG. 27 is a second illustration for explaining operation of the vein keeper. FIG. 28 is a third illustration for explaining operation of the vein keeper. FIG. 29 is an illustration of a bipolar cutter viewed from the top surface of the tip part of the bipolar cutter. FIG. 30 is a cross-sectional view of the bipolar cutter of FIG. 29. FIG. 31 is an exploded perspective view of a tip part of a modified bipolar cutter. FIG. 32 is an illustration of the bipolar cutter viewed from the top surface. FIG. 33 is an illustration of the bipolar cutter viewed from the under surface. FIG. 34 is a cross-sectional view of the bipolar cutter taken along the line XXXIV-line XXXIV of FIG. 32. FIG. 35 is a cross-sectional view of the bipolar cutter taken along the line XXXV-line XXXV of FIG. 32. FIG. 36 is an illustration of a tissue holding part viewed from the under surface. FIG. 37 is a cross-sectional view of the tissue holding part taken along the line XXXVII-line XXXVII of FIG. 36. FIG. 38 is a cross-sectional view of the tissue holding part taken along the line XXXVIII-line XXXVIII of FIG. 36. FIG. 39 is an illustration for explaining cutting operation of a branch with a modified bipolar cutter. FIG. 40 is an illustration for explaining the cutting operation of the branch with a modified bipolar cutter. FIG. 41 illustrates the tissue holding part viewed from the under surface at a time of cutting the branch. FIG. 42 illustrates an external appearance of a disposable dissector. FIG. 43 illustrates an external appearance of a disposable harvester.

First, with reference to FIG. 1 through FIG. 6, a system for pulling and harvesting a subcutaneous vessel as a living body tissue, and an operating method for harvesting a blood vessel using a living body harvesting surgery system will be described.

As shown in FIG. 1, a living body harvesting surgery system (hereinafter may be referred to as surgery system) 101 includes a trocar 21, a dissector 31, a harvester 41 and a rigid endoscope 51 which is a endoscope. The dissector 31 and the harvester 41 are living body tissue harvesting devices. The surgery system 101 further includes a television monitor 102, which is a display device, a camera control unit (hereinafter referred to as CCU) 103, a television camera device 104, a light source device 105, a light guide cable 106, an electric knife device 107, and a gas supplying device 108.

To a light guide connector part 52 of the rigid endoscope 51, an end of the light guide cable 106 is connected. The other end of the light guide cable 106 is connected to the light source device 105. To the rigid endoscope 51, light from the light source device 105 is provided through the light guide cable 106 into which a light guide of optical fiber is inserted, and a subject is illuminated from the tip part of the rigid endoscope 51. A camera head part of the television camera device 104 is connected to an eyepiece part 53 of a base end side of the rigid endoscope 51. The television camera device 104 is connected to the CCU 103, and an image of the subject obtained by the rigid endoscope 51 is displayed on a screen of the television monitor 102.

A tip insertion section 54 of the rigid endoscope 51 can be inserted into a rigid endoscope insertion channel 36 from a base end side of the dissector 31 which is the living body tissue harvesting device. Similarly, the tip insertion section 54 of the rigid endoscope 51 can be inserted into a rigid endoscope insertion channel 46 of the harvester 41 which is the living body tissue harvesting device from a base end side of the harvester 41. The rigid endoscope insertion channels 36 and 46 are mounting parts for mounting the endoscope 51 to the insertion section of the dissector 31 and the harvester 41 respectively, and constitute endoscope insertion means.

A gas supplying tube 34 of the dissector 31 is connected to the gas supplying device 108, a predetermined gas, for example, carbon dioxide gas, is supplied from the gas supplying device 108, and the gas is discharged from an opening 35a (not shown in FIG. 1) which is a gas supplying outlet of the insertion section.

A gas supplying tube 44 of the harvester 41 is also connected to the gas supplying device 108, a predetermined gas, for example, carbon dioxide gas, is supplied from the gas supplying device 108, and the gas is discharged from an opening (not shown in FIG. 1) which is a gas supplying outlet of the insertion section. The gas supplying tubes 34 and 44 respectively constitute gas supplying means inside of the insertion sections of the dissector 31 and the harvester 41.

The harvester 41 has an electrical cable 47 for the bipolar cutter 43 (not shown in FIG. 1). The harvester 41 is connected to the electric knife device 107 by a connector provided at a base end side of the electrical cable 47.

By using the surgery system 101 having the structure, as will be described below, the operator can perform an operation in which a subcutaneous vessel as a target living body tissue to be harvested is pulled and harvested. First, by using the dissector 31, circumferential tissues of great saphenous vein (hereinafter may be referred to as blood vessel) from a thigh of a lower limb to an ankle is dissected, and then, by using the harvester 41, peripheral branches are cut. After the operation is performed, the end part of the blood vessel is treated and the blood vessel is extracted. As described the above, under endoscopic observation, the living body tissues are harvested.

As shown in FIGS. 2 and 3, the trocar 21 includes a guiding tube part 22 which is a guide sheath, a seal member 23, and a fixing part 24 for fixing the trocar 21 to the skin. The guiding tube part 22 has a cylindrically-shaped hollow part 25 through which the insertion sections 32 and 42 of the dissector 31 and the harvester 41 can be inserted. The tip side of the guiding tube part 22 has a shape which is cut away at a predetermined angle, for example, an angle of forty-five degrees, to a direction orthogonal to the axis direction of the guiding tube 22. The base end side of the guiding tube part 22 has a shape which is cut away in a direction orthogonal to the axis direction of the guiding tube 22. At the base end side of the guiding tube part 22, a seal member 23 is provided. The seal member 23 is made of an elastic member, and has a hole 26 which has an inside diameter smaller than that of the guiding tube member 22. In the inner circumference of the hole 26, a convex part 27 is provided at the tip side so that the inner diameter at the tip end side becomes smaller than that at the base end side. By thus shaped hole 26, the insertion section 32 of the dissector 31 or the insertion section 42 of the harvester 41 which is inserted into the guiding tube part 22 can be held in an airtight state under the skin.

On a peripheral surface of the guiding tube part 22 of the trocar 21, a clip member 29 which uses elastic force of a torsion spring 28 which is an elastic member, is provided. The clip member 29 has a plate shape formed in a dogleg shape having a tip part 29a and a base end part 29b. At substantially central part of the dogleg-shaped plate, the torsion spring 28 is provided.

By the torsion spring 28, the tip part 29a of the clip member 29 is always in a pressed state toward the peripheral surface of the guiding tube part 22. The tip part 29a can be apart from the peripheral surface of the guiding tube part 22 by depressing the base end part 29b of the clip member 29 against the pressure of the torsion spring 28. Thus, by depressing the base end part 29b of the clip member 29 toward the side of the peripheral surface of the guiding tube part 22, it is possible to hold skin of a lower limb 12, or the like between the tip part 29a of the clip member 29 and the peripheral surface of the guiding tube part 22 (see FIGS. 6 and 8).

On the peripheral surface of the guiding tube part 22, a plurality of circularly round convex parts 22a is provided. The convex part 22a can be provided by being integrally formed with the guiding tube part 22 or provided as a different member from the guiding tube part 22. On the peripheral surface of the guiding tube part 22 of the tip part 29a of the clip member 29, catching part 29c is formed. Thus, as shown in FIGS. 6 and 8, in the state that the skin of the lower limb 12, or the like is held between the tip part 29a of the clip member 29 and the peripheral surface of the guiding tube part 22 by the pressure of the torsion spring 28, the skin of the lower limb 12, or the like is tightly held and fixed by the catching part 29c of the clip member 29 and the peripheral surface of the guiding tube part 22. Accordingly, the catching part 29c and the convex part 22a of the guiding tube part 22 constitute a fixation part 24 which has a so-called non-slip mechanism.

In the above-structured surgery system 101, in a bypass operation of heart, it is possible to harvest the blood vessel to be used as a harvesting target tissue of the lower limb. With reference to FIG. 4 through FIG. 9, a case in which an entire great saphenous vein (hereinafter, may be referred to as blood vessel), which is the harvesting target blood vessel used for bypass, is harvested from a thigh of the lower limb to an ankle will be described. In the embodiment, according to an example of routine shown in the flowchart in FIG. 4, the above-described blood vessel harvesting operation using the living body harvesting surgery system 101 will be described.

As shown in FIG. 5, a harvesting target blood vessel 11 exists between an inguinal region 13 of a lower limb 12 and an ankle 14. The length of the blood vessel 11 to be harvested is, for example, 60 cm.

First, the operator identify the position of the blood vessel 11 (step (hereinafter, referred to as S) 1). The position of the blood vessel 11 is identified by a tactile impression of the operator or by using a device such as sonar. Then, in a direction substantially along the tube of the blood vessel 11, right above the identified blood vessel 11 and slightly below a knee 15, the operator provides an incision part 16, for example, having the length of 2.5 cm, by a surgical knife, or the like (S2). Then, at the incision part 16, the blood vessel 11 is exposed and peripheral tissues of the blood vessel 11 are dissected (S3).

Next, by using the dissector 31, the peripheral tissues of the entire length of the blood vessel 11 are dissected (S4). Specifically, the operator sets the trocar 21 to the incision part 16, inserts the dissector 31 through a guiding tube part 22 of the trocar 21, while watching the endoscopic image, gradually inserts the dissector 31 from the incision part 16 in the direction to the inguinal region 13 (indicated by the arrow A1), and bluntly dissects the blood vessel 11 from the peripheral tissues. The endoscopic image is necessary for the operator to dissect the peripheral tissues along the blood vessel 11.

When dissecting the peripheral tissues of the blood vessel 11, for example, if it is considered that the direction of the skin surface from the blood vessel 11 is an upward direction, the operator can completely dissect the peripheral tissues from the entire circumference of the blood vessel 11 by dissecting in the upward and downward directions of the blood vessel 11, and further rightward and leftward directions of the blood vessel. By dissecting the entire circumference of the blood vessel 11, it is possible for the operator to watch the branches of the blood vessel 11 more clearly in the endoscopic image.

When the dissecting of the blood vessel 11 from the peripheral tissues in the inguinal region 13 direction is completed, the dissector 31 is pulled from the trocar 21. Then, the direction of the trocar at the incision part 16 is changed, and the dissector is gradually inserted from the incision part 16 in the direction to the ankle 14 (indicated by the arrow A2), and the blood vessel 11 is dissected from the peripheral tissues while watching the endoscopic image.

As shown in FIG. 3, when the trocar 21 is set to the incision part 16, the operator inserts the guiding tube part 22 from the incision part 16 in the direction to the inguinal region, and fixes to the skin by the fixing part 24. The insertion section 32 of the dissector 31 is inserted into the subcutaneous of the lower limb 12 through the guiding tube part 22 of the trocar 21 fixed to the incision part 16 by the fixing part 24.

As will be described below, an endoscope insertion section is inserted into the insertion section 32. Since the insertion direction of the dissector 31 is along the direction of the blood vessel 11, the operator gradually inserts the dissector 31 while watching the endoscopic image so as to dissect the peripheral tissues of the blood vessel 11 from the blood vessel 11. That is, the insertion is not performed to directly reach the inguinal region 13 from the incision part 16 along the blood vessel 11. By moving the dissector 31 forward and backward along the insertion direction, the dissectings of the blood vessel 11 is gradually performed to the inguinal region 13 and to the ankle 14.

Then, by a gas supplying connector provided to the dissector 31, a predetermined gas, for example, carbon dioxide gas, is supplied from a gas supplying tube 34 connected to a grip section 33 of the dissector 31, and blown out from an opening part 35a provided at the tip part of the insertion section 32.

Accordingly, while the blood vessel 11 is dissected from the peripheral tissues, the predetermined gas, for example, carbon dioxide gas, exists between the dissected tissues and the blood vessel, and the operating field of the endoscope is broadened and the visibility is improved. Thus, the operator is able to perform the dissecting operation easily.

Then, the operator pulls the dissector 31 from the trocar 21, while the trocar 21 is left, inserts the harvester 41 (see FIG. 8), and cuts the branches of the blood vessel 11 from the incision part 16 to the ankle 14 (S5).

When the operator cuts the branches 11A, first, inserts the harvester 41 from the incision part 16 to below the ankle 14, and in the direction from the ankle 14 to the incision part 16, cuts the branches 11A one by one.

The cutting of the branches 11A is performed by using a bipolar cutter 43 which is an electric knife provided at a tip part of the insertion section 42 of the harvester 41. The cut part of the branches 11A cut by the bipolar cutter 43 become substantially stanched state. By using the harvester 41, all of the branches 11A of the blood vessel 11 to the ankle 14 are cut.

A structure of the harvester 41 will be described below in detail. A brief structure will now be described. A vein keeper 45 is a blood vessel holding part provided at the tip part of the harvester 41 to hook the blood vessel 11. The vein keeper 45 of the harvester 41 has a mechanism that when the operator hooks the blood vessel 11 to the vein keeper 45, a part of the vein keeper 45 is opened and the blood vessel 11 is hooked to the opened part, after the blood vessel 11 is hooked, the opened part is closed. Further, since the vein keeper 45 is movable in the axis direction of the harvester 41, and it is possible to move the vein keeper 45 in the direction separating from the tip part of the endoscope, the hooked blood vessel 11 can be seen easier in the endoscopic image.

Further, at the tip part of the bipolar cutter 43, a groove of 0.5 mm width is formed. When the branch 11A is cut, the branch 11A is pushed into the groove and cut in a compressed state. Moreover, at the tip part of the harvester 41, on the inside of surrounded part surrounded by a wiper guard part, a wiper for wiping extraneous matters adhered on a window part of the tip part of the rigid endoscope is provided. And, on a part of the cylindrical wiper guard, a sweeping hole for sweeping the extraneous matters wiped by the wiper is provided. As the extraneous matters, blood, fat, smoke due to the electric knife or the like can be considered.

The harvester 41 is also provided with a gas supplying connector, carbon dioxide gas is supplied from a gas supplying tube 44 connected to a grip section 400 of the harvester 41, and blows out from an opening part (not shown) provided at the tip part of the insertion section 42. Accordingly, the cutting operation of the branches 11A becomes easier.

Since a plurality of the branches 11A exists in the blood vessel 11, while watching the endoscopic image at the tip of the insertion section 42 of the harvester 41, the operator holds the blood vessel 11 by operating the vein keeper 45 of the tip part of the harvester 41, confirms the branches 11A one by one, and cuts the branches 11A by the bipolar cutter 43. A structure of the vein keeper 45 will be described below.

Then, a treatment of the distal end is performed by providing a small incision part, for example, the length of the incision part is not greater than 1 cm, on the ankle 14, the distal end of the blood vessel 11 is pulled from the incision part 17, and the distal end is tied with a piece of string or indwelled with forceps (S6). In this case, the operator inserts the harvester 41 near the incision part 16 again into the subcutaneous of the ankle 14, and while watching the subcutaneous vessel 11 under the incision part 17 and the forceps by using the endoscope, pinches the blood vessel 11 with the forceps, and pulls the blood vessel 11 from the incision part 17.

FIG. 7 is an illustration for explaining the treatment of the distal end of blood vessel 11. The treatment of the distal end of blood vessel 11 is performed by tying a part of the blood vessel 11 with a piece of string, and cutting the blood vessel 11 at a position 11b which is nearer to knee 15 than the knot 11a. The incision part at the incision part 17 is closed by the operator with a tape or the like.

In the treatments of the distal end of the blood vessel 11, the operator pulls the blood vessel 11 from the incision part 17 while watching the subcutaneous vessel under the incision part 17 by the endoscope.

Then, the harvester 41 is pulled from the trocar 21, the direction of the guiding tube part 22 of the trocar 21 in the incision part 16 is changed to the direction to the inguinal region 13, the harvester 41 is inserted, and branches of the blood vessel 11 between the incision part 16 and the inguinal region 13 are cut (S7). As performed in S6, the operator cuts the branches 11A of the blood vessel 11 from the incision part 16 to the inguinal region 13 while watching the endoscopic image.

Also, the cutting operation of the branches 11A is performed by inserting the harvester 41 from the incision part 16 into under the inguinal region 13, from the inguinal region 13 toward the incision part 16, the branches 11A of the blood vessel 11 are cut one by one.

As shown in FIG. 8, the insertion section 42 of the harvester 41 is inserted into the subcutaneous of the lower limb 12 through the guiding tube part 22 of trocar 21 fixed to the incision part 16 by the fixing part 24. As will be described below, an endoscope insertion section is inserted into the insertion section 42. Since the insertion direction of the harvester 41 is along the direction of the blood vessel 11, the operator cuts the branches 11A while watching the endoscopic image.

When the cutting operation of the branches 11A of the blood vessel 11 is completed, as shown in FIG. 7, the treatment of the distal end is performed by providing a small incision part, for example, the length of the incision part is not greater than 1 cm, on the inguinal region 13, the distal end of the blood vessel 11 is pulled from the incision part 18, and the distal end is tied with a piece of string or indwelled with forceps (S8).

Also in this case, the operator inserts the harvester 41 near the incision part 16 again into the subcutaneous of the inguinal region 13 while watching the subcutaneous vessel 11 under the incision part 18 and the forceps by the endoscope, pinches the blood vessel 11 with the forceps, and pulls the blood vessel 11 from the incision part 18. Similarly to the treatment at the incision part 17 of the ankle 14, the treatment of the distal end of blood vessel 11 is performed by tying a part of the blood vessel 11 with a piece of string, and cutting the blood vessel 11 at a position 11d which is nearer to knee 15 than the knot 11c. The incision part at the incision part 18 is closed by the operator with a tape or the like.

Then, as shown in FIG. 9 the operator extracts the blood vessel 11, for example, the length is 60 cm, from the incision part 16 (S9). When the extraction of the blood vessel 11 is completed, then, the operator performs a leak check of the blood vessel 11 because if there is an opening on the extracted blood vessel 11, it is not possible to use the blood vessel 11 as a blood vessel to be used for a bypass (S10).

While performing the leak check, the operator ties all of the branches 11A of the blood vessel 11 with a piece of string in order to prevent the cut distal end parts of the branches 11A from blood leaking. In the state in which all of the branches 11A are tied with a piece of string, in consideration of the direction of valves in the blood vessel 11, a syringe is attached to an end of the blood vessel 11, physiological saline is passed through in the blood vessel 11, and by checking whether there is an opening from which the physiological saline is leaking or not, the operator performs the leak check of the blood vessel 11.

If there is an opening from which the physiological saline is leaking, the opening is stitched together (S11). Finally, the incision part 16 is stitched together (S12).

As described above, compared with a known operation in which tissues of a certain part of the lower limb 12 are incised so that the entire blood vessel 11 from the inguinal region 13 of the lower limb 12 to the ankle 14 can be seen, the above-described method for extracting the blood vessel by using the endoscope is minimally invasive to a patient because, for example, the incision parts are only three. It can be possible, for example, to reduce the period of time required for the patient to become able to walk after the operation.

Referring to FIG. 10 through FIG. 16, a structure of the dissector 31 will be described. As shown in FIG. 5, the dissector 31 mainly includes an insertion section 32 and a grip section 33 connected to the insertion section 32. At the tip part of the insertion section 32 which is made of metal, a dissecting member 37 is provided. The dissecting member 37 is made of a material such as a transparent synthetic resin, and has a cylindrical shape at the base end side and a cone shape at the tip side. Since the dissecting member 37 is a transparent member, when subcutaneously inserted, it is possible to obtain an image of a subject illuminated by light illuminated from the tip part of the rigid endoscope 51 inserted into a rigid endoscope insertion channel 36 by using the rigid endoscope 51.

As shown in FIG. 11 through FIG. 14, along an axis direction of the dissector 31, a metal tube member 36a which forms the rigid endoscope insertion channel 36 is inserted through the inside of the dissector 31 from the base end of the grip section 33 to the tip part of the insertion section 32. At the tip side of the grip section 33, a substantially column-shaped first connecting member 38 is provided. Specifically, the grip section 33 is a hollow cylindrical outer member, and on the inner circumference surface of the outer member at the tip side of the grip section 33, the outer circumferential surface of the first connecting member 38 is contacted and fit through a sheath 39.

At an end surface 38b of the base end side of the first connecting member 38, the gas supplying tube 34 is connected. On the first connecting member 38, a hole 38c which communicates an inside space of the gas supplying tube 34 with an inside space of the metal sheath 39 is formed. The hole 38c is a communication path between the inside space of the gas supplying tube 34 and the inside space of the metal sheath 39. An opening part 38d of the hole 38c is provided on the tip side surface of the first connecting member 38. That is, at an end of the hole 38c, the gas tube 34 is fit in the grip section 33, another end of the hole 38c is inside of the metal sheath 39, and opens within an outside space 39a of the tube member 36a. At the base end of the gas supplying tube 34, a gas supplying connector 34a is provided. The gas supplying connector 34a is connected to a connector of a tube connected to the gas supplying device 108. Thus, the gas supplying device 108 can supply a predetermined gas in the sheath 39 through the gas supplying tube 34 and the hole 38c of the first connecting member 38.

The dissecting member 37 and the sheath 39 of the insertion section 32 are connected by a second connecting member 58a. The dissecting member 37 fits at the tip side of the second connecting member 58a, and the sheath 39 fits at the base end side of the second connecting member 58a. Accordingly, the insides of the dissecting member 37 and the sheath 39 are combined together to be airtight.

At the base end side of the second connecting member 58a, three hook-shaped parts 58b which protrude toward the base end side are formed. The tip side of the hook-shaped part 58b has a convex part 58c extends in a direction radiating from the central axis in a plane orthogonal to the axis direction of the insertion section 32. On the sheath 39, holes 35 are formed at a position corresponding to each of the tip parts of the three hook-shaped parts 58b. The hole 35 of the sheath 39 of the insertion section 32 is formed so as to catch the convex part 58c. Further, sizes of each convex part 58c and hole 35 are set to form a space between the hole 35 and the convex part 58c in the state that the convex part 58c is caught in the hole 35. Thus, three openings 35a are formed. An outer diameter of the second connecting member 58a at the base end side is larger than that of the sheath 39.

Accordingly, the carbon dioxide gas supplied from the gas supplying tube 34 is introduced into the air-tight space 39a formed by the sheath 39, the tube member 36a, the first connecting member 38, and the second connecting member 58a through the hole 38c of the first connecting member 38. The introduced gas is blown out from the air-tight space 39a to the outside of the insertion section 32 through the opening part 35a.

As shown in FIG. 15, in order to facilitate and ensure the fixation of the rigid endoscope 51 to the base end part 33a of the dissector 31, a guiding groove 33b is provided on the inner circumference surface of a base end part 33a of the dissector 31 in the direction along the axis of the dissector 31. Further, to the guiding groove 33b, a fixing member 33c is screwed. The fixing member 33c is formed by bending a plate-shaped member made of metal into U-shape, further bending the both ends of the U-shape toward the inside of the U-shape so as to have convex-shaped parts. On the other hand, at a tip side of an eyepiece 53 of the rigid endoscope 51, a convex part 52a (see FIG. 10) is provided.

Further, a notched part 33d is provided on the base end part 33a and a light guide connector part 52 can move along the notched part 33d.

When the operator inserts the rigid endoscope 51 from the base end part of the dissector 31, inserts the rigid endoscope 51 so that the convex part 52a enters along the guiding groove 33b provided on the inner circumference surface of a base end part 33a, and the light guide connector part 52 enters along the notched part 33d. When the rigid endoscope 51 is being inserted from the base end of the dissector 31, the convex part 52a is moved along the inside of the guiding groove 33b, and moved ahead of the convex-shaped part of the fixing member 33c made of metal against the elastic force of the fixing member 33c. Then, the light guiding connector part 52 is also moved along the notched part 33d provided on the base end part 33a.

Accordingly, when the rigid endoscope 51 is inserted from the base end part of the dissector 31, the positional relationship between the dissector 31 and the rigid endoscope 51 is set so that the light guide connector part 52 enters the notched part 33d and the convex part 52a enters the guiding groove 33b, and then, the rigid endoscope 51 is inserted into the dissector 31. When the rigid endoscope 51 is inserted into the dissector 31, the convex part 52a of the rigid endoscope 51 is engaged and fixed in a sandwiched manner by the fixing member 33c in the middle of the insertion, and the convex part of the rigid endoscope 51 becomes not readily fallen off by the elastic force of the fixing member 33c.

Further, when the convex part 52a is engaged and fixed, between the rigid endoscope 51 and the dissector 31, sound implying that the rigid endoscope 51 is engaged arise, and the user can confirm by the sound that the rigid endoscope 51 is set.

With reference to FIG. 16, an arranging relationship between the first connecting member 38 and the tube member 36a which is made of metal and forms the rigid endoscope insertion channel 36 in the grip section 33 will be described in detail. As shown in FIG. 16, the tip side of the tube member 36a is fixed to the second connecting member 58a and the base end side of the tube member 36a is fixed to a part of the base end side of the grip section 33. A central axis of the tube member 36a whose both ends are fixed is, as shown in FIGS. 11 and 16, arranged on the same axis AX as the central axis of the insertion section 32, and the tube member 36a is inserted through the central part of the first connecting member 38. As shown in FIG. 16, although the tube member 36a is inserted through a hole 38e in the central part of the first connecting part 38, a space 38f is provided between the inner circumference surface of the hole 38e and the outer circumference surface of the tube member 36a. The space 38f constitutes a communication path which communicates with an inner space of the sheath 39 and an inner space of the grip section 33.

That is, the tube member 36a is loosely inserted through the hole 38e of the first connecting member 38.

Since a space 38f having an interval of d3 is provided between the inner circumference surface of the hole 38e and the outer circumference surface of the tube member 36a, the inner space of the sheath 39 communicates with the inner space of the grip section 33 through the space 38f.

Further, on the outer member of the grip section 33, a space 33e which is a part from which the gas supplying tube 34 is inserted inside, and other spaces are provided. As the other spaces, for example, there is a hole (not shown) provided on the outer member of the grip section 33. Such holes constitute a communication path which communicates the inner space with the outer space of the grip section 33.

Thus, the inner space of the sheath 39 communicates with the outer space of the grip section 33 through the space 38f and the space 33e.

According to the above structure, the carbon dioxide gas supplied through the gas supplying tube 34 is introduced into the inner space of the sheath 39 through the hole 38c of the first connecting member 38. The carbon dioxide gas is discharged from the hole 35a into a body cavity. By the introduction of the carbon dioxide into the body cavity, pressure in the body cavity increases. However, through the space 38f and the space 33e which communicate with the inner space of the sheath 39 and the outer surface of the grip section 33, the carbon dioxide in the body cavity is discharged.

Accordingly, in the case in which the carbon dioxide is supplied into the body cavity by controlling the supplying amount of the carbon dioxide supplied from the gas supplying tube 34 to be a predetermined amount, if the pressure in the body cavity is increased, the carbon dioxide in the sheath 39 is discharged to the outside space of the grip section 33 through the space 38f and the space 33e. Thus, the space 38f and the space 33e which form at least a part of the communication path, by releasing the carbon dioxide gas in the body cavity, constitutes pressure reducing means for reducing, that is, releasing the pressure in the body cavity so as to prevent the pressure from becoming beyond a predetermined pressure. The predetermined pressure is determined by a relationship between a flow rate of the gas supply or the like and a cross-sectional area of each space. A part having the smallest cross-sectional area of the communication path is set to have a smaller cross-sectional area than a part having the smallest cross-sectional area of the gas supplying path. That is, the part having the smallest cross-sectional area of the gas supplying path is set to have a larger cross-sectional area than the part having the smallest cross-sectional area of the communication path.

With reference to FIG. 17 through FIG. 24, a structure of the harvester 41 will be described. As shown in FIG. 17, the harvester 41 mainly includes the insertion section 42 and a grip section 400 connected to the insertion section 42. On a tip part of the insertion section 42 of the harvester 41 which is a cylindrical tube made of metal, the bipolar cutter 43 is provided at its upper part and the vein keeper 45, which is a holder, is provided at the inside of its lower part. If a bipolar cutter lever 401 and a vein keeper lever 402 provided on a grip section 400 which is consecutively provided to the base end of the insertion section 42, are moved forward and backward in the direction along the longitudinal direction, in conjunction with the movements, the bipolar cutter 43 and the vein keeper 45 can be moved forward and backward ahead of the insertion section 42.

As to a structure of the base end side of the harvester 41, as shown in FIG. 18, the structure is similar to that of the base end side of the dissector 31 (see FIG. 15). Specifically, in the structure of the base end side of the harvester 41, as shown in FIG. 18, a guiding groove 400b is provided on the inner circumference surface of a base end part 400A of the harvester 41 in the direction along the axis of the harvester 41 in order to facilitate and ensure the fixation of the rigid endoscope 51 to the base end part of the harvester 41. Further, to the guiding groove 400b, a fixing member 400c is screwed. The fixing member 400c is formed by bending a plate-shaped member made of metal into U-shape, further bending the both ends of the U-shape toward the inside of the U-shape so as to have convex-shaped parts.

Further, a notched part 400d is provided on the base end part 400A and a light guide connector part 52 can move along the notched part 400d.

When the rigid endoscope 51 is inserted from the base end part of the harvester 41, the rigid endoscope 51 is inserted so that the convex part 52a of the rigid endoscope 51 is entered along the guiding groove 400b provided on the inner circumference surface of a base end part 400A shown in FIG. 9, and the light guide connector part 52 is entered along the notched part 400d. When the rigid endoscope 51 is being inserted from the base end of the harvester 41, the convex part of the rigid endoscope 51 is moved along the inside of the guiding groove 400b, and moved ahead of the convex-shaped part of the metal fixing member 400c against the elastic force of the fixing member 400c. Then, the light guiding connector part 52 is also moved along the notched part 400d provided on the base end part 400A.

Accordingly, when the rigid endoscope 51 is inserted from the base end part of the harvester 41, the positional relationship between the harvester 41 and the rigid endoscope 51 is set so that the light guide connector part 52 enters the notched part 400d and the convex part 52a of the rigid endoscope 51 enters the guiding groove 400b, and then, the rigid endoscope 51 is inserted into the harvester 41. When the rigid endoscope 51 is inserted into the harvester 41, the convex part 52a of the rigid endoscope 51 is engaged and fixed in a sandwiched manner by the fixing member 400c in the middle of the insertion, and the convex part 52a of the rigid endoscope 51 is not readily fallen off by the elastic force of the fixing member 400c.

Further, when the convex part 52a of the rigid endoscope 51 is engaged and fixed, between the rigid endoscope 51 and the harvester 41, sound implying that the rigid endoscope 51 is engaged arise, and the user can confirm by the sound that the rigid endoscope 51 is set.

As shown in FIG. 19, the vein keeper 45 of the harvester 41 is composed of a vein keeper axis 412 which holds a substantially U-shaped blood vessel holding base 411 to be movable forward and backward in the longitudinal axis direction, and a lock axis 414 which is movable forward and backward in the longitudinal axis direction against the blood vessel holding base 411 which forms a closed space 413 housing the blood vessel on the substantially U-shaped blood vessel holding base 411 which is parallel to the vein keeper 412. The lock axis 414, in a state shown in FIG. 19, forms the closed space 413 in a state locked to the blood vessel holding base 411 as well as the vein keeper axis 412. However, by releasing the locked state of the lock axis 414, as shown in FIG. 20, it is possible to release the closed space 413 and the lock axis 414 can move forward and backward capable of housing the blood vessel 11 in the closed space 413.

On the tip side surface of the insertion section 42 on which the bipolar cutter 43 is provided, a notch 415 is provided and a bipolar axis (described below) which moves the bipolar cutter 43 forward and backward is inserted into the insertion section 42 through the notch 415. On the inner wall surface of the notch 415, a guard part 416 having an arch-shaped cross section is provided and on the inner surface of the tip of the insertion section 42, a wiper 417 for wiping an extraneous matter adhered to a window part of the tip part of the rigid endoscope 51 is provided. The wiper guard part is formed with an end of the wiper 417 as an axis and the other end for sweeping the inside of the guard part 416.

At one part of the cylindrically-shaped wiper guard part, a sweeping hole 419a for sweeping the extraneous matter 418 (see FIG. 21) wiped by the wiper 417 is provided. As the extraneous matter 418, blood, fat, smoke due to the electric knife or the like can be considered. The wiper 417 sweeps by operating a wiper lever 419 (see FIG. 17) through a wiper axis (not shown, see FIG. 25). As shown in FIG. 21 which is an illustration viewed from the direction of the arrow A of FIG. 19, at a position inside from the tip surface of the insertion section 42 by a predetermined distance, an opening of a rigid endoscope insertion channel 420 in which the rigid endoscope 51 is inserted and an opening of a gas supplying channel 421 are adjacently provided.

As shown in FIG. 22, along the axis direction of the harvester 41, a metal tube member 420a which forms the rigid endoscope insertion channel 420 is inserted inside the harvester 41 from the base end side of the grip section 400 to the tip part of the insertion section 42. In the middle, inside of the insertion section 42 of the metal tube, a plurality of holding members 42a is arranged. The bipolar cutter 43 is connected to the bipolar cutter lever 401 provided on the grip section 400 by a bipolar axis 450 which is inserted through the insertion section 42. If the bipolar cutter lever 401 is moved forward and backward along the longitudinal axis, the force of the movement is transmitted to the bipolar cutter 43 through the bipolar axis 450, and it is possible to move the bipolar cutter 43 forward and backward ahead of the insertion section 42.

Similarly, the vein keeper 45 is connected to the vein keeper lever 402 provided on the grip section 400 by a vein keeper axis 412 which is inserted through the insertion section 42. If the vein keeper lever 402 is moved forward and backward along the longitudinal axis, the force of the movement is transmitted to the vein keeper 45 through the vein keeper axis 412, and it is possible to move the vein keeper 45 forward and backward ahead of the insertion section 42.

A metal tube 420b which forms the rigid endoscope insertion channel 420 is fixed in the insertion section 42 by a plurality of holding members 42a (see FIG. 25). The two bipolar axes 450, the vein keeper axis 412, the lock axis 414, and the wiper axis are not fixed in the insertion section 42 (see FIG. 25). The two bipolar axes 450, the vein keeper axis 412, and the lock axis 414 are configured to be movable forward and backward in the longitudinal axis direction of the insertion section 42, and the wiper axis is configured to be rotatable about the wiper axis.

The vein keeper lever 402 and the vein keeper axis 412 are integrally movable in the inner surface of the grip section 400 by a click assembly 451 which pin pressing the inner surface of the grip section 400. If the click assembly 451 positions, for example, one of three click grooves 452 provided on the inner surface of the grip section 400, the vein keeper lever 402 and the vein keeper axis 412 can be stably held at the position. If the operator adds force to the longitudinal axis, the click assembly 451 can be readily thrown out from the click groove 452.

The vein keeper lever 402 is removably connected with the lock lever 453, and by depressing a lock button 454, the vein keeper lever 402 can be separated from the lock lever 453. The lock lever 453 is connected with the lock axis 414, and by moving the lock lever 453 forward and backward in a state being separated from the vein keeper lever 402, the lock lever 453 can be moved forward and backward being capable of housing the blood vessel 11 within the closed space 413 (see FIGS. 19 and 20).

As shown in FIG. 23, the vein keeper lever 402 is strongly fixed to the vein keeper axis 412 by screw 460 and gluing.

As shown in FIGS. 24 and 25, along the axis direction of the harvester 41, a gas supplying pipe 461 made of metal and forms a gas supply channel is inserted in the harvester 41 from the base end side of the grip section 400 to the tip part of the insertion section 42. At one end of the gas supplying pipe 461 of the grip section 400, a gas supplying tube 44 is fitted in the grip section 400, a gas supplying connector 44a is provided at a base end of the gas supplying tube 44, and the gas supplying connector 44a is connected to a connector of a tube connected to the gas supplying device 108.

As described above, in the embodiment, as shown in FIG. 26, by moving the vein keeper lever 402 forward and backward, it is possible to move the vein keeper 45 forward and backward at the tip. Accordingly, for example, as shown in an endoscopic image in FIG. 27, if a state of the branch 11A is hard to see when cutting the branch 11A, by moving the vein keeper lever 402 forward in the longitudinal axis direction as shown in FIG. 28, the tip of the vein keeper 45 moves forward, and it is possible to see an endoscopic image suitable for confirming the state of the branch 11A.

With reference to FIGS. 29 and 30, the bipolar cutter 43 which is inserted in the harvester 41 now will be described.

As shown in FIG. 29, the bipolar cutter 43 has a cutter body 422 which is a branch holding member made of a transparent insulating member, an active electrode 425 which is one of electrodes in the bipolar, and a return electrode 424 which is another electrode of the electrodes in the bipolar. As shown in FIG. 30, the bipolar cutter 43 has a three-layered structure formed by an upper layer of the return electrode 424, the cutter body 422, and the active electrode 425.

The cutter body 422 has a v-shaped groove 436 formed at the tip side, and at the base end side of the v-shaped groove 436, a slit groove 427 having, for example, a width of 0.5 mm, is formed.

When the branch 11A is cut, the branch 11A is guided to the slit groove 427 along the v-shaped groove 436 of the cutter body 422, by the branch 11A pushed and entered in the slit groove 427, the branch 11A is held in the slit groove 427 in a compressed state. In the state, by applying a high-frequency current from the active electrode 425 to the return electrode 424, the branch 11A is cut and stanched.

Since a contact area of the return electrode 424 is larger than that of the active electrode 425, the current efficiently concentrates to the active electrode 425, and it is possible to perform the incision part and blood stanching.

Thus constructed bipolar cutter 43 can be manufactured inexpensively while having excellent workability and heat-durability and the blood stanching performance of the living body tissue such as a blood vessel (branch 11A) to be cut can be increased by configuring the bipolar cutter 43 as described below. That is, if in the bipolar cutter 43, the cutter body 422 is entirely made of synthetic resin, the durability may be slightly lost due to heat generated by a discharge between the two electrodes 424 and 425. On the other hand, if the cutter body 422 is made of ceramics having heat-durability, the manufacturing cost is higher and the workability is inferior to the above case.

Moreover, as described above, the bipolar cutter 43 cuts the living body tissue (branch 11A) by a thermal action of the discharge of high-frequency current from the one active electrode 425 to the other return electrode 424. Accordingly, it can be possible to reduce the possibility of damage due to heat without entirely forming the bipolar cutter by using ceramics, but by forming only between the pair of electrodes, particularly, the part of the bipolar cutter which contacts with the active side electrode by using ceramics having heat-durability. That is, in the bipolar cutter, it is preferable to form most of the cutter body by using synthetic resin which is inexpensive and excellent in workability, and provide a ceramics member between the pair of electrodes.

However, ceramics has higher thermal conductivity than synthetic resin such as polycarbonate. Accordingly, in the bipolar cutter, heat generated at the active electrode and the living body tissue to be cut due to the high-frequency current discharged between the pair of electrodes extensively transmits to the member made of ceramics. As a result, the amount of heat consumption at the living body tissue to be cut is reduced at the time of cutting, and the blood stanching performance is reduced.

Accordingly, in consideration of the above problems, the bipolar cutter 43 can be configured as described below.

As shown in FIG. 31 through FIG. 35, the bipolar cutter 43 includes a cutter body 422, a tissue holding part 423, an active electrode 425 which is a first electrode to be one of electrodes in the bipolar, and a return electrode 424 which is a second electrode to be another electrode of the electrodes in the bipolar, two lead wires 428 (an active side lead wire 428a, a return side lead wire 428b), and a lead wire cover 426.

The cutter body 422 is made of, as described above, for example, a synthetic resin which is a transparent insulating member such as polycarbonate. The cutter body 422 has, when viewed from the axis in the longitudinal direction, a cross section curved in arch-shape (see FIG. 35) so as to fit the arch-shaped inner circumference surface of a notch part 415 (see FIGS. 21 and 22) in the harvester 41.

The cutter body 422 includes a v-shaped groove 436 formed at the tip, a fitting part 435 in which the tissue holding part 423 is fitted (described below), a groove part 422*j* in which the lead wire 428*a* of the active side and the lead wire 428*b* of the return electrode side are arranged respectively in an insulated state, and the lead wire cover 426*a* is fitted, and a concave part 422*l* on which the return electrode 424 is arranged. At the bottom surface of the groove part 422*j*, two long grooves are formed through the entire length of the groove part 422*j* to retain the insulated state between the lead wire 428*a* of the active side and the lead wire 428*b* of the return side.

The fitting part 435 is composed of a first groove part 435*a* formed in slit-shape from the v-shaped groove 436 at the tip of the cutter body 422, and a second groove part 435*b* formed in substantially circular shape at the base end side when viewed from upward direction.

Further, to the cutter body 422, a step part 422*a* (see FIGS. 32 and 35) to be an inward flange at the inner circumference surface where a fitting part 435 is to be formed and on the position corresponding to the base end of the tissue holding part 423, a concave groove part 422*b* for fitting (see FIGS. 31 and 34) is formed.

To the groove in which the lead wire of the active side of the groove part 422*j* is arranged, a penetration part 422*e* (see FIGS. 32 and 33) in which a lead wire connecting part 425*a* of the active electrode 425 is inserted at the tip side, is provided. Accordingly, at the active electrode 425 arranged at the under surface side of the cutter body 422, the lead wire connecting part 425*a* is inserted into the penetration part 422*e*, and the end part of the lead wire connecting part 425*a* and the lead wire 428*a* of the active side arranged on the upper surface of the groove part 422*j* come to be electrically connectable.

Further, the cutter body 422 has three fastening parts 422*c* on the upper surface and under surface, two of the fastening parts 422*c* upwardly protrude at the tip side of the concave part 422*l*, and the one fastening part 422*c* downwardly protrudes. These fastening parts 422*c* are inserted into hole parts 425*b* and 424*a* pierced in the active electrode 425 and the return electrode 424. After the fastening parts 422*c* are melted, for example, by thermal caulking, and the fastening parts 422*c* coagulate in outer flange shape (see FIGS. 34 and 35), the return electrode 424 and the active electrode 425 are respectively fixed on the upper and under surfaces of the cutter body 422.

The return electrode 424 is a metal plate which has a curved cross section when viewed along the upper surface of the concave part 422*l* of the cutter body 422 from the longitudinal axis direction. The return electrode 424 has a notched part notched in keyhole-shape and the above-described two hole parts 424*a* when viewed from a boundary of the cutter body 422 and the upper surface of the tissue holding part 423, that is, substantially along each boundary. Moreover, the return electrode 424 has a lead wire connecting part 424*b* electrically connected with a return side lead wire at the base end part by welding and a protruding part 424*c* juxtaposed with the lead wire connecting part 424*b* and fitted and held in the groove part 422*j* of the cutter body 422.

Further, the lead wire connecting part 424*b* and the protruding part 424*c* are bent down below substantially at a right angle respectively, further, bent substantially at a right angle so as to extend toward the base end side. The lead wire connecting part 424*b* is longer in the extending length toward the base end side than the extending length of the protruding part 424*c*, and has an enough length for the welding connection with the return side lead wire.

The protruding part 424*c* is shorter in the extending length toward the base end side than the length from the base end of the concave part 422*l* of the cutter body 422 to the penetration part 422*e* of the groove part 422*j*. Thus, the insulation is retained without the protruding part 424*c* contacting with the lead wire connecting part 425*a* of the active electrode 425 and the active side lead wire 428*a*, and the insulation between the return electrode 424 and the active electrode 425 is also held.

The active electrode 425 is a substantially rectangular-shaped metal plate arranged on the under surface side of the cutter body 422 and the tissue holding part 423, and has the above-described hole part 425*b*. From the active electrode 425, as described above, the lead wire connecting part 425*a*, which is electrically connected with the active side lead wire 428*a* by welding, extends toward the base end side. In the lead wire connecting part 425*a*, the end part in the extending direction is upwardly bent at substantially right angle and further, the end part is bent at substantially right angle in the extending direction.

The active side lead wire 428*a* and the return side lead wire 428*b* are respectively arranged in parallel in two long grooves formed on the bottom surface of the groove part 422*j* of the cutter body 422 so as to be insulated, and electrically connected with the external electric knife device 107 (see FIG. 2).

The tissue holding part 423 is arranged at substantially center of the tip part of the cutter body 422, and made of ceramics which is a heat-resistant member. That is, if the cutter body 422 is entirely made of ceramics, the manufacturing cost is higher than that of synthetic resin, and inferior in workability. Therefore, in the bipolar cutter 43 according to the embodiment, only the tissue holding part 423 is made of ceramics having heat-resistance to reduce the manufacturing cost and has excellent workability.

The tissue holding part 423 is formed in so-called keyhole-shape as shown in FIG. 38 through FIG. 40, and has a cylindrically-shaped part 423A formed in substantially cylindrical shape at the base end part, and a rectangular-shaped part 423B extending from the peripheral side surface of the cylindrically-shaped part 423A and in which a slit groove 427 is formed. The tissue holding part 423 shown in FIG. 26 illustrates the surface to be under surface side when inserted in the cutter body 422.

As shown in FIG. 35, the tissue holding part 423 extends along the longitudinal axis direction, and has two arm parts 423*a* each outwardly protruding from both side surfaces of the rectangular-shaped part 423B, and convex part 423*b* protruding from the side circumference surface of the base end part of the cylindrically-shaped part 423A toward the base end side.

The tissue holding part 423 is fitted into the fitting part 435 of the cutter body 422, the two arm parts 423*a* are held in the step part 422*a* of the first groove part 435*a*, and the convex part 423*b* is fitted and held in the concave part for fitting 422*b* of the cutter body 422. Thus, the tissue holding part 423 is fitted to the cutter body 422.

Further, in the tissue holding part 423, a substantially circumferentially-shaped groove part 440 is formed in the cylindrically-shaped part 423A. As shown in FIG. 33, the groove part 440 is separated by a predetermined distance from the substantially tip part of the active electrode 425 which covers the base end part of the slit groove 427, surrounds the tip part of the active electrode 425 as if drawing a circle, and a bottomed groove formed, for example, in a width of about 0.5 mm and a depth of 1 to 2 mm. It is not limited that the groove 440 is formed in the substantially circumferential shape, any shape, for example, polygonal shape such as rectangular, or triangle can be possible as long as the groove part 440 is separated by the predetermined distance from the substantially tip part of the active electrode 425 which covers the base end part of the slit groove 427. Moreover, the width and depth of the groove part 440 are set so that the tissue holding part 423 can maintain a predetermined strength.

The slit groove 427 is provided by being grooved in the longitudinal direction of the tissue holding part 423 from the tip central part of the substantially rectangular-shaped part 423B to the substantially central part of the substantially cylindrical part 423A, for example, in a width of 0.5 mm.

The tissue holding part 423 is made of a high-heat-resistant ceramics structural material, for example, zirconia or alumina.

On the under surface of the tissue holding part 423, a step part 430 which is notched toward the base end side so as to position the tip part of the active electrode 425 is formed.

In the harvester 41, if ceramics which has higher thermal conductivity than synthetic resins such as polycarbonate is used for the bipolar cutter 43, the heat generated at the active electrode 425 and the branch 11A serving as the living body tissue to be cut due to the high-frequency current discharged between the electrodes 424 and 425 extensively transmits to the tissue holding part 423 made of ceramics. As a result, the amount of heat consumption at the branch 11A is reduced at the time of cutting, and the blood stanching performance is reduced. However, the bipolar cutter 43 according to the embodiment can solve the above problems by the groove part 440 of the tissue holding part 425 formed of ceramics between the electrodes 424 and 425.

A cutting operation of the branch 11A by using thus configured bipolar cutter 43 of the harvester 41 will be described in detail with reference to the flowchart in FIG. 4 and FIG. 39 through FIG. 41. As described above according to the flowchart of FIG. 4, after the peripheral tissues of the entire length of the blood vessel 11 are dissected by using the dissector 31 (S4), then, the dissector 31 is pulled out from the trocar 21, while the trocar 21 is being left, the harvester 41 is inserted, and a cutting operation of the branches 11A of the blood vessel 11 from the incision part 16 to the ankle 14 is performed (S5).

During the operation, the operator operates the bipolar cutter lever 401 of the harvester 41 in the direction the bipolar cutter 43 moves forward so that the branch 11A enters the v-shaped groove 436 of the cutter body 422 while confirming the endoscopic image. By the operation, the branch 11A is guided into the slit groove 427 of the tissue holding part 423 by the v-shaped groove 436.

The operator confirms that the branch 11A is entered into the slit groove 427 and as shown in FIG. 39, the branch 11A is in contact with the active electrode 425 by the endoscopic image, and applies a high-frequency current from the electric knife device 107. Then, the high-frequency current discharged form the active electrode 425 discharges to the return electrode 424 through the branch 11A.

At the part the branch 11A in the slit groove 427 of the tissue holding part 423 and the active electrode 425 in contact with each other, heat is generated due to the discharge from the active electrode 425 and as shown in FIG. 40, the branch 11A coagulates and is cut.

With reference to FIG. 41, a flow of the conduction of the heat generated at the branch 11A to which the high-frequency current form the active electrode 425 is applied, and conducted to the tissue holding part 423 will be described.

In the description below, a side surface of the groove part 440 of the inner circumference side of the tissue holding part 423 is a wall surface 440*a*, a side surface of the outer circumference side is 440*b*, and the part where the active electrode 425 and the branch 11A come in contact with each other is a heat generating part 480.

As described above, the amount of heat generated at the branch 11A is radially conducted to the tissue holding part 423 and conducted to the groove part 440. The amount of heat conducted to the groove 440 depends on thermal conductivity λ of the tissue holding part 423 and the groove part 440.

Heat flow flux qa of the tissue holding part 423 from the heat generating part 480 to the wall surface 440*a* can be calculated according to the formula (1).

$$qa = \lambda a(th - twh)/\delta 1 \quad \text{formula (1)}$$

qa: heat flow flux
λa: thermal conductivity of the tissue holding part 423
th: temperature at the interface between the tissue holding part 423 (slit groove 427) and the branch 11A
twh: temperature at the interface between the wall surface 440*a* and air
δ1: distance from the slit groove 427 in contact with the branch 11A to the wall surface 440*a*

On the other hand, a heat flow flux qb of the groove 440 between the wall surfaces 440*a* and 440*b* of the tissue holding part 423 can be calculated according to the formula (2).

$$qb = \lambda \text{air}(twh - tc)/\delta 2 \quad \text{formula (2)}$$

λair: thermal conductivity of air
tc: temperature at the interface between the wall surface 440*b* and air
δ1: distance from the wall surface 440*a* to the wall surface 440*b*

As will be understood from the formulas (1) and (2), the value of the heat flow flux q depends on the value of the thermal conductivity λ which is a product value. That is, as compared to the thermal conductivity ka of the tissue holding part 423 made of ceramics, the thermal conductivity λair of air is extremely small. Accordingly, the heat flow flux qb at the groove part 440 depends on the value of the thermal conductivity λair of air which is a product value, as compared to the heat flow flux qa of the tissue holding part 423, the heat flow flux qb at the groove part 440 becomes extremely small.

As a result of the above, in the tissue holding part 423, the amount of heat consumption increases at a part from the heat generating part 480 (a part of the slit groove 427) which holds the branch 11A to which heat is supplied from the active electrode 425 to the groove part 440. That is, in the tissue holding part 423, rapid heat conduction is reduced by the groove part 440, and only the part from the heat generating part 480 to the groove 440 comes to have a high temperature. Accordingly, the blood stanching performance of the branch 11A increases due to the increased heat consumption of the branch 11A.

Therefore, in the bipolar cutter 43 according to this embodiment, it is possible to prevent the durability decreasing due to the heat generated by discharge by forming only the part between the pair of electrodes 424 and 425, especially, the part which is in contact with the active electrode 425 by using ceramics without forming the entire of the bipolar cutter 43 using ceramics.

That is, in the tissue holding part 423, the heat conduction from the groove part 440 to the part of the outer circumference side becomes difficult because the groove part 440 is provided. As a result, at the part from the groove part 440 to the part of the outer circumference side in the tissue holding part 423, the rapid temperature increase can be reduced. Accordingly, the temperature increase in the cutter body 422 in which the tissue holding part 423 is inserted can be also reduced. Therefore, even if the cutter body 422 is made of synthetic resin whose working temperature is low, heat durability can be ensured.

The groove part 440 is formed by being notched from the surface (in the embodiment, under surface) of the tissue holding part 423 on which the active electrode 425 is arranged. Accordingly, the amount of heat concentrating around the active electrode 425 which comes in contact with the branch 11A and conducting to the tissue holding part 423 is reduced due to the groove part 440. Therefore, the temperature in the vicinity of the active electrode 425 becomes the highest due to the amount of heat the tissue holding part 423 consumes, as described above, and the amount of heat necessary for the blood stanching of the branch 11A is ensured.

As a result, the bipolar cutter 43 of the harvester 41, which is the cutting means in the embodiment, is excellent in heat durability and can cut the branch 11A of the harvesting target blood vessel 11, which is a living body tissue, while the blood stanching is ensured.

As described above, in order to retain a creepage distance for insulation for withstanding voltage, the central part of the return electrode 424 is notched in substantially round shape substantially around the base end part of the slit groove 427 so that a distance from the tip part of the active electrode 425 positioned at the base end side of the slit groove 427, that is, the heat generating part 480, to the return electrode 424 becomes substantially equal.

Accordingly, the heat generated in the active electrode 425 is conveyed substantially uniformly to the tissue holding part 423 by providing the surface of the tissue holding part 423 on the side of the return electrode 424 in substantially round shape to correspond to that of the return electrode 424, that is to say, to match the surface shape of the cylindrically-shaped part 423A of the tissue holding part 423.

As a result, on the upper surface side of the tissue holding part 423 to be a contact surface between the cutter body 422 and the return electrode 424, and the active electrode 425, it is possible to reduce partial high temperature. That is, on the upper surface of the tissue holding part 423, since the heat generated in the heat generating part 480 is equally conducted, it is possible to prevent the cutter body 422 and the tissue holding part 423 from having a high temperature.

In this embodiment, the tissue holding part 423 made of ceramics in which the groove part 440 is formed at the tip central part of the cutter body 422 is provided. However, all tip parts of the cutter body 422 between the return electrode 424 and the active electrode 425 can be formed with ceramics member having the groove part 440.

Further, λair, the thermal conductivity of air, is affected by the atmosphere temperature. However, since the amount of heat consumption against the branch 11A increases, the discharging time of the high-frequency current from the active electrode 425 to the return electrode 424 can be reduced.

As shown in FIGS. 42 and 43, in this embodiment, the dissector 31 is integrally formed with the gas supplying tube 34 and the gas supplying connector 34a. Further, the harvester 41 is integrally formed with the electrical cable 47, the connector 470 provided at the base end of the electrical cable 47, the gas supplying tube 44 and the gas supplying connector 44a. Thus, in the surgery system 101 according to this embodiment, the dissector 31 and the harvester 41 can be structured to be disposable.

As to the harvester 41, the harvester 41 is configured to release the carbon dioxide gas outside so that the pressure in the body cavity does not exceed a predetermined value when the carbon dioxide gas supplied from the gas supplying tube 44 is supplied into the body cavity from the gas supplying channel 421. More particularly, as shown in FIG. 25, the plurality of holding members 42a are arranged inside of the insertion section 42 which is a tube member. As described above, in the insertion section 42, the metal tube 420b is fixed to the holding members 42a but the other contents, the two bipolar axes 450, the vein keeper axis 412, the lock axis 414, and the wiper axis are not fixed. That is, the two bipolar axes 450, the vein keeper axis 412, the lock axis 414, and the wiper axis are loosely inserted into the plurality of holes provided in the holding members 42a. Accordingly, in each hole, the space 42b is formed between the contents.

The supplied carbon dioxide gas is supplied into the body cavity from the gas supplying channel 421, and the body cavity is communicated with the inner space of the grip section 400 through the above-described space 42b in the insertion section 42. That is, the space 42b constitutes a communication path for communicating the outer space of the insertion section 42 with the inner space of the grip section 400.

Further, on the outer member of the grip section 400, a space 400a as a part for inserting the gas supplying tube inside, and other spaces are provided. The other spaces are, for example, holes provided on the outer member of the grip section 400 (not shown). These spaces constitute a communication path for communicating the inner space with the outer space of the grip section 400.

Accordingly, the inner space of the insertion section 42 is communicated with the outer space of the grip section 400 through the space 42b and the space 400a.

According to the above structure, the carbon dioxide gas supplied through the gas supplying tube 44 is introduced into the body cavity from the tip part of the insertion section 42 through the gas supplying channel 421. By the introduction of the carbon dioxide gas into the body cavity, pressure in the body cavity increases. However, from the tip part of the insertion section 42, the carbon dioxide gas in the body cavity is discharged through the above-described space 42b and the space 400a.

Thus, while controlling the supplying amount of the carbon dioxide supplied from the gas supplying tube 44 to be a predetermined amount, if the carbon dioxide is supplied into the body cavity and the pressure in the body cavity is beyond a predetermined pressure, the carbon dioxide gas is discharged to the outer space of the grip section 400 from the tip part of the insertion section 42 through the space 42b and the space 400a. Accordingly, the space 42b and the space 400a which form at least a part of the communication path, by releasing the carbon dioxide gas in the body cavity, constitutes pressure reducing means for reducing, that is, releasing the pressure in the body cavity so as to prevent the pressure from becoming beyond the predetermined pressure. The predetermined pressure is determined by a relationship between a flow rate of the gas supply or the like and a cross-sectional area of each space. A part having the smallest cross-sectional area of the communication path is set to have a smaller cross-sectional area than a part having the smallest cross-sectional area of the gas supplying path. That is, the part having the smallest cross-sectional area of the gas supplying path is set to have a larger cross-sectional area than the part having the smallest cross-sectional area of the communication path.

As described above, by using the dissector 31 and the harvester 41 according to this embodiment, even when harvesting the subcutaneous vessel such as great saphenous vein under endoscopic observation, it is possible to control the gas pressure in the body cavity so that the pressure does not increase beyond the predetermined pressure.

Second Embodiment

A second embodiment of the present invention will be described. In the above-described structure according to the first embodiment, through the space 38f and the space 33e which communicate with the inner space of the sheath 39 and the outer space of the grip section 33 of the dissector 31, the carbon dioxide in the body cavity is discharged. In a living body tissue harvesting apparatus according to the second embodiment, as shown in FIG. 44 through FIG. 46, a channel for discharge is provided to the insertion section of the dissector 31 to positively discharge the carbon dioxide gas.

Figure 44:
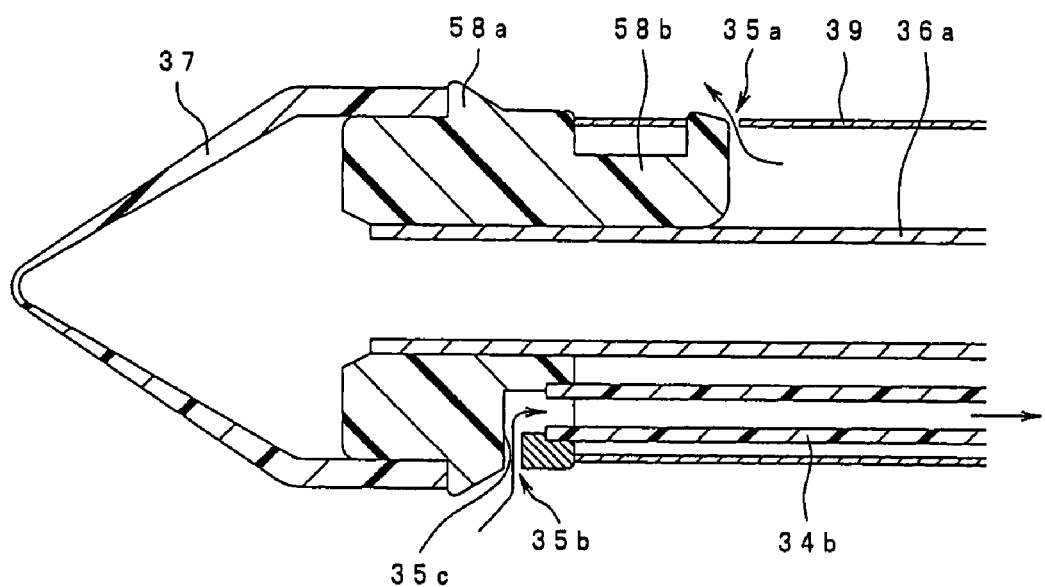
FIG. 44 is a partial cross-sectional view of a tip part of an insertion section according to a second embodiment of the present invention.
Figure 45:
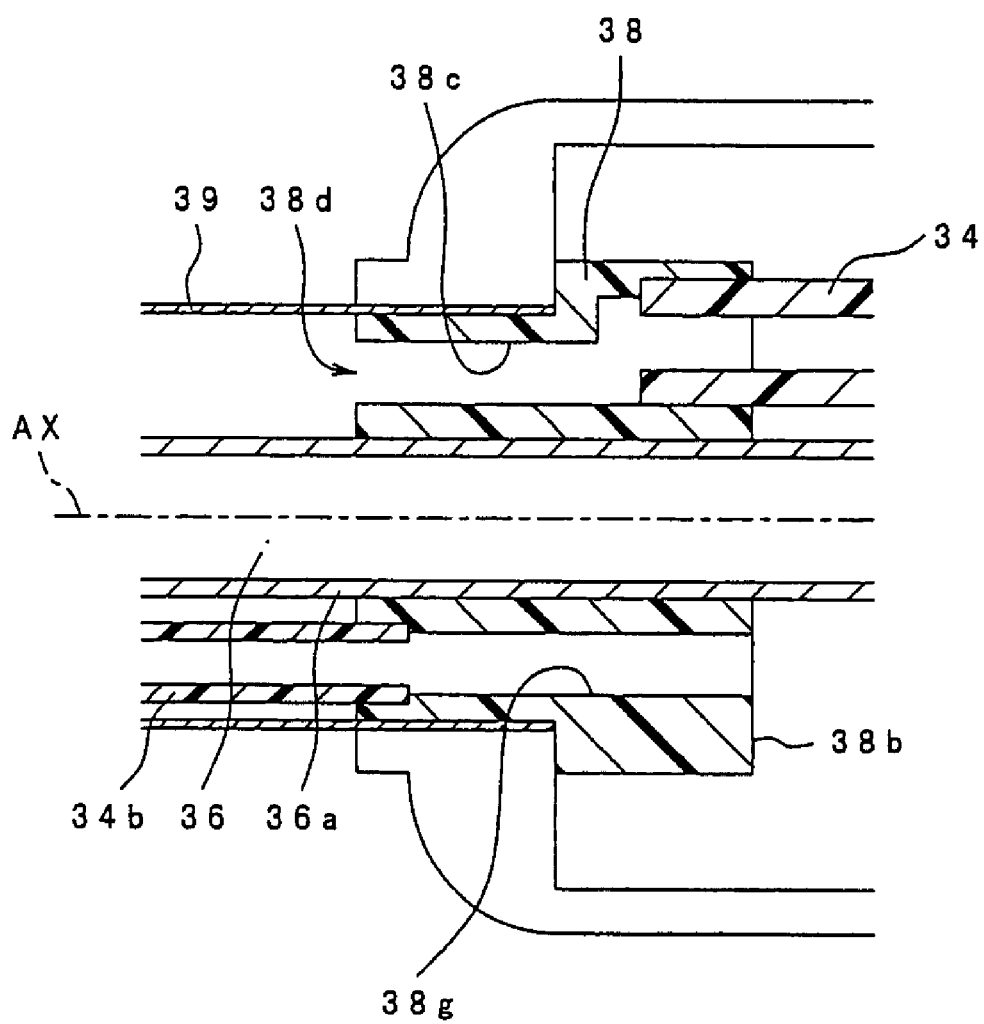
FIG. 45 is a partial cross-sectional view of a tip part of a grip section according to the second embodiment of the present invention.
Figure 46:
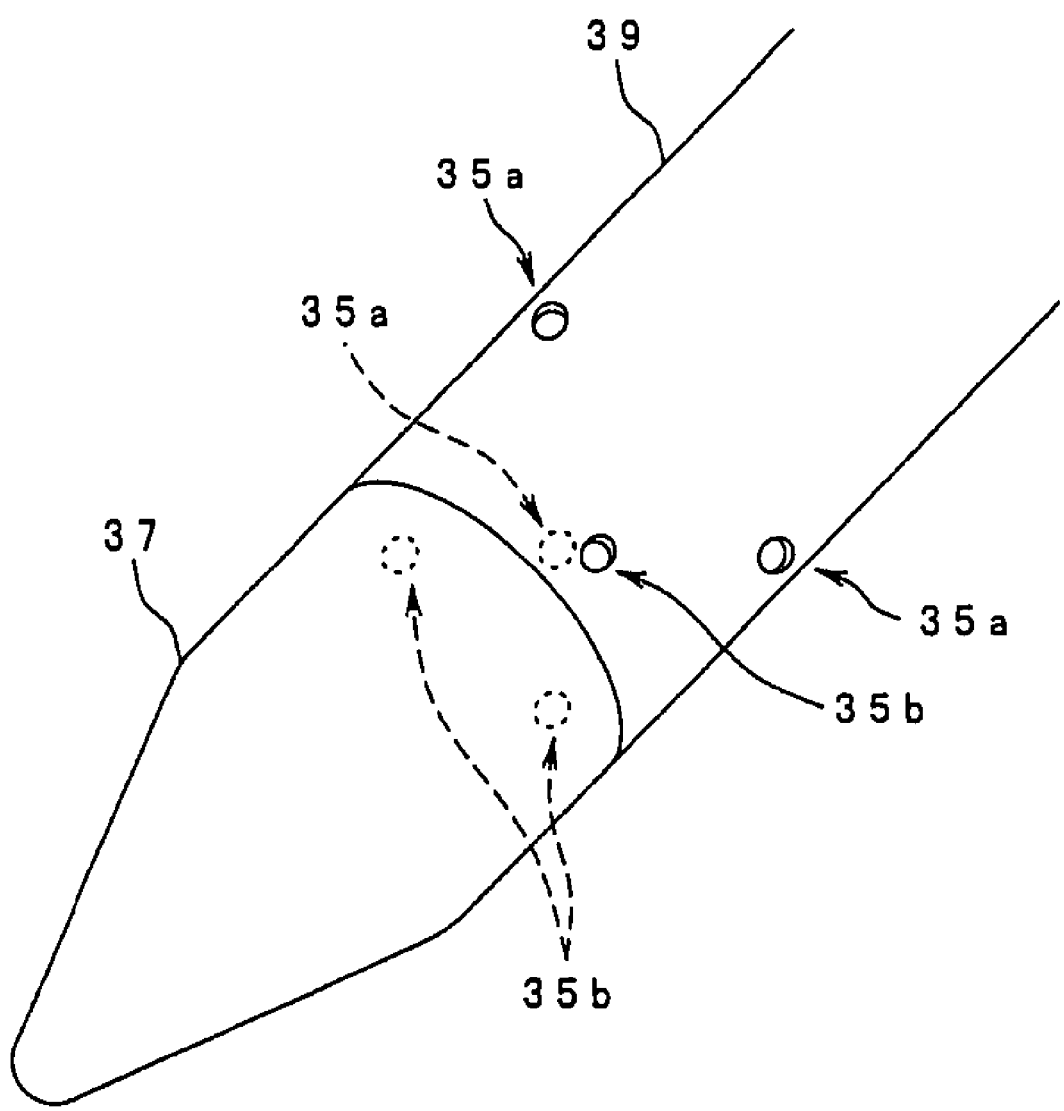
FIG. 46 is an illustration for explaining a position of an opening part of each hole in the insertion section according to the second embodiment of the present invention.

FIG. 44 through FIG. 46 illustrate the structure according to the second embodiment of the present invention. FIG. 44 is a partial cross sectional view of the tip part of the insertion section 32 along the insertion axis. FIG. 45 is a partial cross sectional view of the tip part of the grip section 33 along the insertion axis. FIG. 46 illustrates positions of opening parts of each hole in the insertion section 32. In the FIG. 44 through FIG. 46, the same numbers are given to the constituents corresponding to the constituents described in the first embodiment, and detailed description is omitted in this embodiment.

As shown in FIG. 44, to the second connecting member 58a, more than one hole 35c which has an opening part 35b on the outer circumference surface is provided. In this embodiment, three holes 35c are provided. In particular, each hole 35c is formed in the direction from the outer circumference toward the inner circumference of the second connecting member 58a, and in the middle of the second connecting member 58a, toward the base end side of the insertion section 32. Accordingly, the hole 35c has a substantially L-shape. To the base end side of the second connecting member 58a, a discharge tube 34b which constitutes a discharge channel communicating with the inner space of the hole 35c is connected.

On the other hand, as shown in FIG. 45, the base end side of the discharge tube 34b is connected to the tip surface of the first connecting member 38. To the first connecting member 38, a hole 38g is formed from the tip surface toward the base end surface. One end of the discharge tube 34b is connected to an opening part of the hole 38g of the tip side of the first connecting member 38. The hole 35c, the discharge tube 34b, and the hole 38g constitute a communication path communicating the outer space of the insertion section 32 with the inner space of the grip section 33.

FIG. 46 is a partial perspective view illustrating the positions of the openings 35a and 38g formed on the tip part of the insertion section 32. The three opening parts 35a are provided on the sheath 39 at intervals of angle of 120 degrees around the central axis of the insertion section 32 along the periphery direction. Similarly, three opening parts 35b are provided on the second connecting member 58a at intervals of angle of 120 degrees around the central axis of the insertion section 32 along the periphery direction.

These three opening parts 35b are separated from each opening part 35a by a predetermined distance in the axis direction of the insertion section 32, and arranged at a position rotated by a predetermined angle, for example, 60 degrees, around the central axis of the insertion section 32 so that each opening part 35b and opening parts 35a do not overlap each other when viewed from the axis direction of the insertion section 32.

According to the above structure, the carbon dioxide supplied from one gas supplying tube 34 is supplied into the body cavity from the three opening parts 35a, from the three opening parts 35b through the three discharge tubes 34b and spaces 33e, discharged to the outer space of the grip section 33. Accordingly, the communication path at least a part of which is formed by the hole 35c, the discharge tube 34b, and the hole 38g, by releasing the carbon dioxide gas, constitutes pressure reducing means for reducing, that is, releasing the pressure in the body cavity so as to prevent the pressure from becoming beyond a predetermined pressure. The predetermined pressure is determined by a relationship between a flow rate of the gas supply or the like and cross-sectional areas of the inner channels of these three discharge tubes 34b. A part having the smallest cross-sectional area of the communication path is set to have a smaller cross-sectional area than a part having the smallest cross-sectional area of the gas supplying path. That is, the part having the smallest cross-sectional area of the gas supplying path is set to have a larger cross-sectional area than the part having the smallest cross-sectional area of the communication path.

In the above description, in the structure of the dissector 31, the case in which the channels for discharging the carbon dioxide are positively provided in the insertion section is described. Similarly, in the harvester 41, a channel for discharging carbon dioxide can be positively provided in the insertion section.

Third Embodiment

A third embodiment of the present invention will now be described. In the structures according to the above-described the first and second embodiments, carbon dioxide in the body cavity is discharged through the space 38f and the space 33e which are communicating with the inner space of the sheath 39 and the outer of the grip section 33 of the dissector 31, or the channels provided on the insertion section. A living body tissue harvesting apparatus according to the third embodiment, as shown in FIG. 47, has a relief valve 200 in the middle of the gas supplying tube 34.

Figure 47:
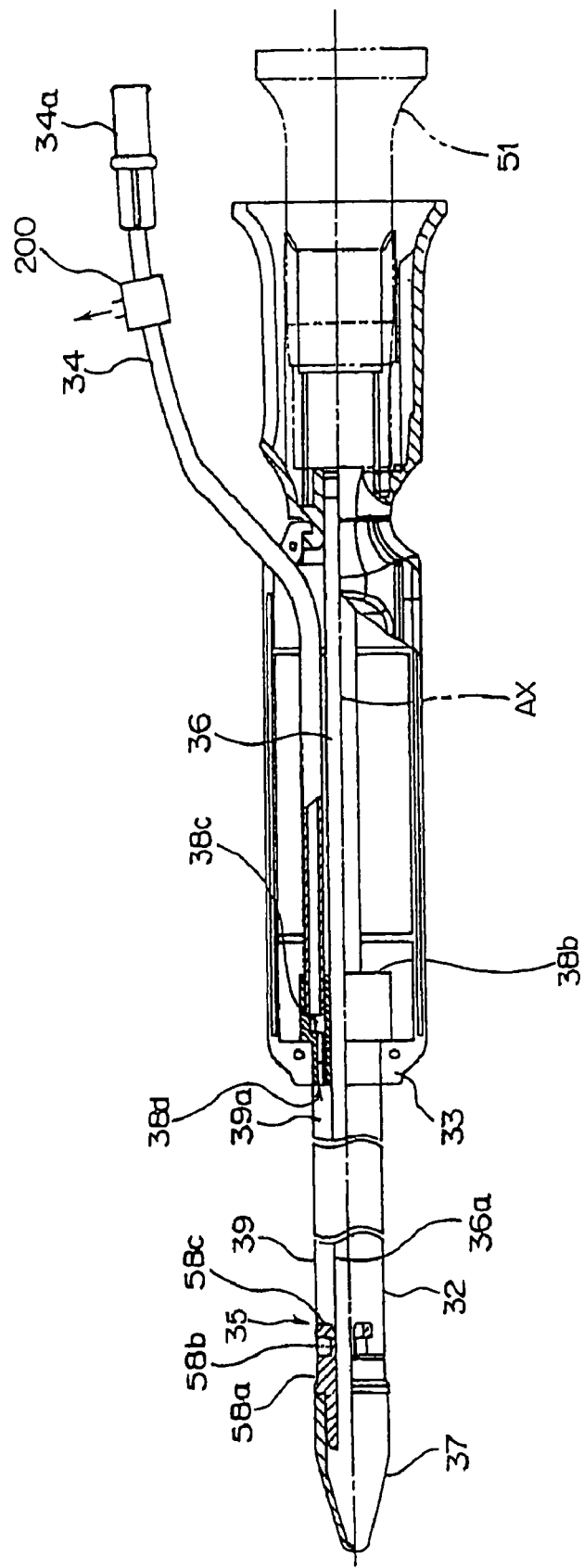
FIG. 47 is a partial cross-sectional view of a dissector according to a third embodiment of the present invention.

FIG. 47 is an illustration for explaining the structure according to the third embodiment of the present invention. FIG. 47 is a partial cross-sectional view of the dissector 31 according to the third embodiment of the present invention. In FIG. 47, the same numbers are given to the constituents corresponding to the constituents described in the first embodiment, and detailed description is omitted in this embodiment.

As shown in FIG. 47, since the relief valve 200 is provided in the middle of the gas supplying tube 34, if pressure in the relief valve 200 exceeds a pressure set at the relief valve 200, carbon dioxide gas in the gas supplying tube 34 is discharged. Therefore, the pressure in the body cavity does not become beyond the predetermined pressure. Because the relief valve 200 releases the carbon dioxide gas, pressure reducing means for reducing, that is, releasing the pressure in the body cavity so as to prevent the pressure from becoming beyond the predetermined pressure, is composed. The relief valve 200 can be provided on the base end side of the sheath 39 of the insertion pert 32. By providing the relief valve 200 on the base end side of the sheath 39, if the pressure in the airtight space 39a becomes beyond the predetermined pressure, the carbon dioxide gas in the airtight space 39a is discharged.

In the above description, in the structure of the dissector 31, the case in which the relief valve 200 is provided to the gas supplying tube 34 or the sheath 39 of the insertion section 32 is described. Similarly, in the harvester 41, the relief valve 200 can be provided in the gas supplying tube 44 or the insertion section 42.

While the present invention has been described with reference to the embodiments, it is to be understood that the invention is not limited to the disclosed embodiments. And various changes and modifications thereof could be made without departing from the spirit and scope of the invention as defined in the appended claims. Further, each of the above embodiments includes the invention at various steps, and by combining a plurality of features, various combination of the invention can be extracted.

For example, even if some features are deleted from the whole features shown in each embodiment, if the problem described in the section of BACKGROUND OF THE INVENTION can be solved, and the advantages described in the section of SUMMARY OF THE INVENTION can be obtained, the structure in which some features are deleted can be extracted as the invention.

What is claimed is:

1. A living body tissue harvesting apparatus for cutting a living body tissue, the living body tissue harvesting apparatus comprising:
 a plate-shaped cutter body made of an insulating member, the cutter body including a base end part and a tip part,;
 a plate-shaped heat-resistant member connected to the cutter body, the plate-shaped heat-resistant member including a first surface and a second surface;
 an active electrode for supplying electric energy, the active electrode being arranged on a first surface side of the heat-resistant member and including a base end part and a tip part;
 a return electrode for receiving electric energy from the active electrode, the return electrode being arranged on a second surface side of the heat-resistant member,
 wherein the heat-resistant member further includes:
  a first groove part for guiding the living body tissue from the tip part of the cutter body, and
  a second groove part for reducing heat conduction that is formed on the first surface side of the heat-resistant member such as to surround a tip part of the active electrode which protrudes from the first groove part.

2. The living body tissue harvesting apparatus according to claim 1, wherein the second groove part is formed on the side of the heat-resistant member that is in contact with the active electrode.

3. The living body tissue harvesting apparatus according to claim 2, wherein the second groove part is formed circularly on the heat-resistant member such as to be separated from the tip part of the active electrode by a predetermined distance.

4. The living body tissue harvesting apparatus according to claim 3, wherein the heat resistant member is substantially cylindrically-shaped at the part thereof held between the active electrode and the return electrode.

5. The living body tissue harvesting apparatus according to claim 2, wherein the heat resistant member is substantially cylindrically-shaped at the part thereof held between the active electrode and the return electrode.

6. The living body tissue harvesting apparatus according to claim 1, wherein the second groove part is formed circularly on the first surface side of the heat-resistant member such as to be separated from the tip part of the active electrode by a predetermined distance.

7. The living body tissue harvesting apparatus according to claim 6, wherein the heat resistant member is substantially cylindrically-shaped at the part thereof held between the active electrode and the return electrode.

8. The living body tissue harvesting apparatus according to claim 1, wherein the heat resistant member is substantially cylindrically-shaped at the part thereof held between the active electrode and the return electrode.

9. A living body tissue harvesting apparatus for cutting a living body tissue, the living body tissue harvesting apparatus comprising:
 an elongated insertion section configured to be inserted in a living body tissue and including a base end part and a tip part, the insertion section including inside thereof an endoscope channel through which an endoscope for observing a living body tissue is insertable in a longitudinal direction, a holder channel through which a holder for holding the living body tissue is insertable in a longitudinal direction, and a cutter channel through which a cutter for cutting the living body tissue is insertable in a longitudinal direction;
 the cutter including:
  a plate-shaped cutter body including a base end part and a tip part and made of an insulating member, the cutter body including a first surface and a second surface;
  an active electrode for supplying electric energy, the active electrode including a base end part and a tip part and arranged on the first surface of the cutter body;
  a return electrode for receiving electric energy from the active electrode, the return electrode being arranged on the second surface of the cutter body; and
  a heat-resistant member arranged to be buried at the tip part of the cutter body and including a plate surface, the heat-resistant member being held between the active electrode and the return electrode and including a first groove part for guiding the living body tissue from a tip part side of the cutter body and a second groove part for reducing heat conduction that is formed on the plate surface of the heat-resistant member such as to surround the tip part of the active electrode which protrudes from the first groove part.

10. The living body tissue harvesting apparatus according to claim 9, wherein the second groove part is formed on the surface of the heat-resistant member that is in contact with the active electrode.

11. The living body tissue harvesting apparatus according to claim 10, wherein the second groove part is formed circularly on the heat-resistant member such as to be separated from the tip part of the active electrode by a predetermined distance.

12. The living body tissue harvesting apparatus according to claim 11, wherein the heat-resistant member is substantially cylindrically-shaped at the part thereof held between the active electrode and the return electrode.

13. The living body tissue harvesting apparatus according to claim 10, wherein the heat resistant member is substantially cylindrically-shaped at the part thereof held between the active electrode and the return electrode.

14. The living body tissue harvesting apparatus according to claim 9, wherein the second groove part is formed circularly on the surface of the heat-resistant member such as to be separated from the tip part of the active electrode by a predetermined distance.

15. The living body tissue harvesting apparatus according to claim 14, wherein the heat-resistant member is substantially cylindrically-shaped at the part thereof held between the active electrode and the return electrode.

16. The living body tissue harvesting apparatus according to claim 9, wherein the heat resistant member is substantially cylindrically-shaped at the part thereof held between the active electrode and the return electrode.

* * * * *